US012735452B2

(12) United States Patent
Bray et al.

(10) Patent No.: US 12,735,452 B2
(45) Date of Patent: Sep. 15, 2026

(54) ADHESIVE PEPTIDES

(71) Applicant: Zentraxa Limited, Bristol (GB)

(72) Inventors: Harriet Eleanor Victoria Bray, Bristol (GB); Martin Richard Challand, Bristol (GB); Paul Raymond Race, Bristol (GB); Robert Christopher Salmon, Bristol (GB)

(73) Assignee: Zentraxa Limited, Bristol (GB)

( * ) Notice: Subject to any disclaimer, the term of this patent is extended or adjusted under 35 U.S.C. 154(b) by 423 days.

(21) Appl. No.: 18/038,936

(22) PCT Filed: Nov. 22, 2021

(86) PCT No.: PCT/EP2021/082509

§ 371 (c)(1),
(2) Date: May 25, 2023

(87) PCT Pub. No.: WO2022/112177

PCT Pub. Date: Jun. 2, 2022

(65) Prior Publication Data

US 2024/0025948 A1 Jan. 25, 2024

(30) Foreign Application Priority Data

Nov. 26, 2020 (GB) ...................................... 2018608

(51) Int. Cl.
*C07K 7/06* (2006.01)

(52) U.S. Cl.
CPC ...................................... *C07K 7/06* (2013.01)

(58) Field of Classification Search
None
See application file for complete search history.

(56) References Cited

U.S. PATENT DOCUMENTS

| | | | |
|---|---|---|---|
| 2017/0015885 | A1 | 1/2017 | Liu et al. |
| 2019/0194290 | A1 | 6/2019 | Wagner, Jr. et al. |

FOREIGN PATENT DOCUMENTS

| | | | |
|---|---|---|---|
| CN | 102559638 | A | 7/2012 |
| EP | 3 339 439 | A1 | 6/2018 |
| JP | H08266282 | A | 10/1996 |
| WO | WO 1988/007076 | A1 | 9/1988 |
| WO | WO 2010/065962 | A2 | 6/2010 |
| WO | WO 2014/191997 | A1 | 12/2014 |

OTHER PUBLICATIONS

International Preliminary Report on Patentability for PCT/EP2021/082509, mailed Feb. 7, 2023 (19 pages).
CN 102559638 A, English Abstract provided.
JP H08266282 A, English Abstract provided.
Venkatareddy et al., "Mussel-Glue Inspired Adhesives: A study on the Relevance of $_L$-Dopa and Function of the Sequence at Nanomaterial-Peptide Interfaces," *Adv Mater. Interfaces* 6:1900501, 2019 (6 pages).
Wei et al., "Bridging Adhesion of Mussel Inspired Peptides: Role of Charge, Chain Length, and Surface Type," *Langmuir* 31:1105-1112, 2015.
Search Report mailed dated May 19, 2021 in GB 2018608.6 (1 page).
International Search Report mailed on Mar. 4, 2022 in PCT/EP2021/082509 (5 pages).
Written Opinion mailed on Mar. 4, 2022 in PCT/EP2021/082509 (5 pages).
Roberts, et al., "Elastin-like polypeptides as models of intrinsically disordered proteins." *FEBS letters* 589(19): 2477-2486, Sep. 2015.
Urry et al., "Elastic-contractile model proteins: Physical chemistry, protein function and drug design and delivery," *Adv. Drug Deliv. Rev.* 62(15): 1404-1455, 2010.
Urry, "Physical chemistry of biological free energy transduction as demonstrated by elastic protein-based polymers." *J. Phys. Chem. B* 101(51):11007-11028, Dec. 1997.

*Primary Examiner* — Sergio Coffa
(74) *Attorney, Agent, or Firm* — Klarquist Sparkman, LLP

(57) ABSTRACT

The invention concerns a plurality of peptides or polypeptides, in, or for use in, an adhesive; ideally said peptides or ploypeptides include at least one, including any combination, of the following sequences: an adhesive sequence, a cross-linking sequence, an elastic conferring sequence, and a de-bonding or cleavable sequence.

16 Claims, 7 Drawing Sheets

Figure 1A:
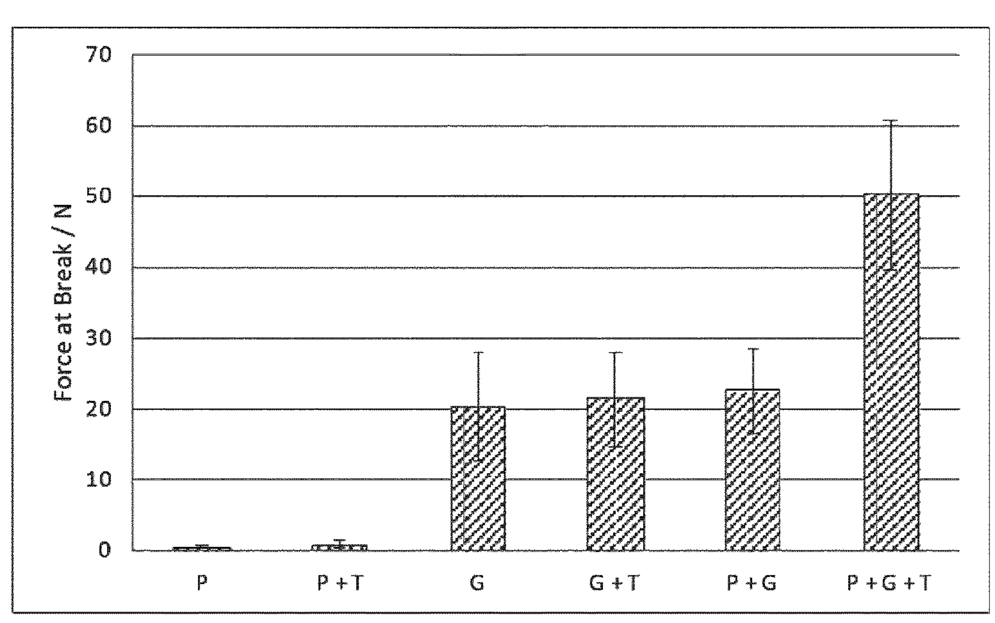

Specification includes a Sequence Listing.

| Peptide name | Sequence nomenclature | Tensile strength/ MPa | Fold improvement in tensile strength over gelatine/ A.U. |
|---|---|---|---|
| ADP6 | [P1]-[A1]-[D9]-[A1] | 0.20 ± 0.05 | 2.67 ± 0.68 |
| ADP7 | [P1]-[A1]-[D4]-[A1] | 0.46 ± 0.08 | 6.20 ± 1.12 |
| AEDP1 | $[A5]_2$-[E1]-[D3]-[E1]-$[A1]_2$ | 0.46 ± 0.03 | 6.15 ± 0.42 |
| AP6 | [P1]-$[A1]_2$ | 0.71 ± 0.03 | 9.54 ± 0.38 |
| ADP5 | [P1]-[A2]-[D9]-[A2] | 0.83 ± 0.21 | 11.1 ± 2.86 |
| AP2 | [P1]-$[A2]_3$ | 0.38 ± 0.05 | 5.08 ± 0.64 |
| AP28 | [P10]-$[A3]_2$-[S11] | 0.25 ± 0.02 | 3.37 ± 0.22 |
| AEP3 | [A3]-[E2]-[A1] | 0.41 ± 0.10 | 5.55 ± 1.37 |
| AEP4 | [A3]-[E3]-[A1] | 0.19 ± 0.02 | 2.51 ± 0.20 |
| ADP8 | [P10]-[A4]-[D9]-[A2]-[S11] | 0.26 ± 0.08 | 3.55 ± 1.07 |
| ADP2 | [P1]-$[A1]_2$-[D3]-$[A5]_2$-[D3]-$[A5]_2$-[S1] | 0.23 ± 0.07 | 3.16 ± 1.00 |
| AP24 | [P5]-$[A6]_2$-[S4] | 0.19 ± 0.03 | 2.60 ± 0.36 |
| AP25 | [P5]-$[A7]_2$-[S4] | 0.27 ± 0.00 | 3.69 ± 0.06 |
| AP30 | [P1]-$[A8]_2$-[A2] | 0.14 ± 0.05 | 1.88 ± 0.71 |
| AP26 | [P10]-$[A6]_2$-[S11] | 0.32 ± 0.08 | 4.38 ± 1.14 |
| AP27 | [P10]-$[A7]_2$-[S11] | 0.34 ± 0.07 | 4.56 ± 0.95 |

| Peptide name | Sequence nomenclature | Tensile strength/ MPa | Fold improvement in tensile strength over gelatine/ A.U. |
|---|---|---|---|
| AP6 | $[P1]-[A1]_9$ | 0.71 ± 0.03 | 9.54 ± 0.38 |
| AP2 | $[P1]-[A2]_3$ | 0.38 ± 0.05 | 5.08 ± 0.64 |
| AP28 | $[P10]-[A3]_2-[S11]$ | 0.25 ± 0.02 | 3.37 ± 0.22 |
| AP24 | $[P5]-[A6]_2-[S4]$ | 0.19 ± 0.03 | 2.60 ± 0.36 |
| AD25 | $[P5]-[A7]_2-[S4]$ | 0.27 ± 0.00 | 3.69 ± 0.06 |
| AP30 | $[P1]-[A8]_2-[A2]$ | 0.14 ± 0.05 | 1.88 ± 0.71 |
| AP26 | $[P10]-[A10]_2-[S11]$ | 0.32 ± 0.08 | 4.38 ± 1.14 |
| AP27 | $[P10]-[A12]_2-[S11]$ | 0.34 ± 0.07 | 4.56 ± 0.95 |

| Peptide name | Sequence nomenclature | Tensile strength/ MPa | Fold improvement in tensile strength over gelatine/ A.U. |
|---|---|---|---|
| AEP3 | [A3]-[E2]-[A1] | 0.41 ± 0.10 | 0.55 ± 1.37 |
| AEP4 | [A3]-[E3]-[A1] | 0.19 ± 0.02 | 2.51 ± 0.20 |

| Peptide name | Sequence nomenclature | Tensile strength/ MPa | Fold improvement in tensile strength over gelatine/ A.U. |
|---|---|---|---|
| ADP7 | [P1]-[A1]-[D4]-[A1] | 0.46 ± 0.08 | 6.20 ± 1.12 |
| ADP5 | [P1]-[A2]-[D9]-[A2] | 0.83 ± 0.21 | 11.1 ± 2.86 |
| ADP2 | [P1]-$[A1]_2$-[D3]-$[A5]_2$-[D3]-$[A5]_2$-[S1] | 0.23 ± 0.07 | 3.16 ± 1.00 |

ADHESIVE PEPTIDES

CROSS REFERENCE TO RELATED APPLICATIONS

This is the U.S. National Stage of International Application No. PCT/EP2021/082509, filed Nov. 22, 2021, which was published in English under PCT Article 21(2), which in turn claims the benefit of GB Application No. 2018608.6, filed Nov. 26, 2020. The PCT application is herein incorporated by reference in its entirety.

FIELD OF THE INVENTION

The invention concerns a plurality of peptides or polypeptides, in, or for use in, an adhesive; ideally said peptides or polypeptides include at least one, including any combination, of the following sequences: an adhesive sequence, a cross-linking sequence, an elastic conferring sequence, and a de-bonding or cleavable sequence.

Incorporation of Electronic Sequence Listing

The electronic sequence listing, submitted herewith as a txt file named sequence.txt (22,252 bytes), created on May 25, 2023, is herein incorporated by reference in its entirety.

BACKGROUND OF THE INVENTION

Mussels produce and secrete natural protein molecules (Mfp5) that function as water-resistant bioadhesives, fixing the mollusc to the seabed. At the end of a secreted thread an adhesive plaque is deposited containing several proteins with high ratios of 3,4-dihydroxyphenyl-L-alanine (DOPA), which is derived from hydroxylation of tyrosine residues. The DOPA content of a mussel adhesive protein is specifically related to its adhesive properties, with mussel adhesive protein analogues lacking DOPA showing greatly reduced adhesion abilities.

Synthetic peptides represent an ideal platform to exploit DOPA-based adhesion. They can be readily synthesised using chemical or recombinant methods which allow for the precise arrangement of the adhesive functional groups. Tyrosine amino acids can be converted to DOPA using a tyrosinase enzyme thus allowing for convenient activation of the adhesive from a non-adhesive precursor peptide. Moreover, additional amino acids can be included in an artificially designed peptide that provides for at least one enhanced or further functionality, such as improved adhesion (e.g. to hydrophobic surfaces) or increased elasticity or resilience of the adhesive material.

These synthetic peptides, advantageously, can be used as medical adhesives because they are often non-toxic to the human body and are non-immunogenic. Moreover, their biodegradable properties make them environmentally friendly. Indeed, peptide degradation can be accelerated through treatment with protease enzymes or chemicals that accelerate peptide bond hydrolysis. This avoids using any harsh conditions, such as UV radiation or high heat.

In reconstituted mussel adhesives, DOPA residues are introduced by producing a protein or peptide containing tyrosine (Y) at the requisite position and then post-translationally converting tyrosine to DOPA, using a tyrosinase enzyme. DOPA residues allow adhesive and cohesive interactions through surface chelation, hydrogen bonding, formation of mono, bi or tri dentate metal ion complexes and through cation-pi interactions with positively charged residues, specifically lysine (K) and arginine (R) resides. Additionally, DOPA residues can enable mussel adhesive protein molecules to cross-link with each other via oxidative conversion to o-quinone. While the covalent interaction is critical to the build up of high molecular weight structures, increasing the cohesive strength of the resulting material, it sacrifices adhesive interactions that occur through the DOPA functional group. However, a lack of cross-links results in molecules slipping past each other and gives rise to a soft material with weak cohesion. It is, therefore, desirable to develop a system that will allow covalent cross-links to develop between peptide chains via a chemistry that does not 'quench' the adhesive DOPA functional group.

The invention described herein concerns a new class of adhesive peptides with the above desirable features.

STATEMENTS OF THE INVENTION

According to a first aspect of the invention there is provided in, or for use in, an adhesive, a plurality of adhesive hexapeptides wherein each one has a motif comprising 3 different amino acids wherein 2 of said 3 amino acids repeat side by side to provide at least one of the following sequence patterns:

XX-YY- or -XX-YY where X, Y and—are any 3 different amino acids.

In a preferred embodiment of the inventions at least two of said adhesive hexapeptides are the same.

Reference herein to a hexapeptide is to a peptide containing 6 amino acids.

Reference herein to am adhesive hexapeptide motif or an adhesive peptide is reference to a peptide sequence that has, or after treatment with an activator such as a tyrosinase, has adhesive properties. Accordingly, prior to said treatment said hexapeptide motif is a precursor peptide adhesive.

Accordingly, the invention comprises a an adhesive polypeptide comprising a plurality of hexapeptides wherein each one has a motif comprising 3 different amino acids wherein 2 of said 3 amino acids repeat side by side to provide at least one of the following patterns:

XX-YY- or -XX-YY where X, Y and—are any 3 different amino acids.

In a preferred embodiment at least two of said adhesive hexapeptides are the same.

In a preferred embodiment, said amino acids are selected from the group comprising: Alanine A, arginine R, asparagine N, aspartic acid D, cysteine C, glutamic acid E, glutamine Q, glycine G, histidine H, isoleucine I, leucine L, lysine K, methionine M, phenylalanine F, proline P, serine S, threonine T, tryptophan W, tyrosine Y, and valine V.

Most preferably the amino acids are naturally occurring L-amino acids but they may also be D-amino acids. D-Amino acids are amino acids where the stereogenic carbon alpha to the amino group has the D-configuration.

In yet a further preferred embodiment said amino acids are selected from the group comprising: glycine G, tyrosine Y, lysine K, alanine A, serine S and arginine R.

More preferably still said hexapeptide comprises one of the following motifs: GYYGKK (SEQ ID NO: 1), AYYAKK (SEQ ID NO: 2), KKGYYG (SEQ ID NO: 3), KKAYYA (SEQ ID NO: 4), GKKGYY (SEQ ID NO: 5), GYYGRR (SEQ ID NO: 6), GYYGSS (SEQ ID NO: 7), AYYARR (SEQ ID NO: 8), AYYASS (SEQ ID NO: 9), RRGYYG (SEQ ID NO: RRAYYA (SEQ ID NO: 11), SSGYYG (SEQ ID NO: 12) and SSAYYA (SEQ ID NO: 13).

The hexapeptide sequences presented in this invention contain a functional (adhesive) domain, the functional domain contains a high ratio of DOPA groups, or their non-adhesive precursor peptide tyrosine (Y), giving the adhesive function.

In addition, increasing the quantity of hydrophobic amino acids provides the potential for additional adhesion and cohesion through hydrophobic interactions and, in particular, gives stronger adhesion when bonding low energy hydrophobic surfaces. Accordingly in certain embodiments of the invention said peptide includes, in addition to tyrosine, amino acids selected from the group comprising amino acids glycine (G), arginine (R), serine (S), lysine (K) and alanine (A) in the functional adhesive domain.

Most preferably a plurality of said hexapeptide motifs are the same and so, ideally, some different hexapeptide motifs are provided.

Moreover, each hexapeptide motif is a functional adhesive domain, and it is flanked by cross-linking domains at the N and/or C termini.

Accordingly, and yet more preferably still, said adhesive peptide comprises an N-terminal and/or C-terminal cross-linking sequence whereby said adhesive hexapeptide is cross-linked with other adhesive hexapeptides to provide peptide chains. Preferably said cross-linking sequence is selected from the group comprising: SGEGKK (SEQ ID NO: 14), SGEGK (SEQ ID NO: 15), GKK, AKAAK (SEQ ID NO: 16), AKA, SSAKAAK (SEQ ID NO: 17), SSAKA (SEQ ID NO: 18), YFKG (SEQ ID NO: 19), LKG, FKG, YLKG (SEQ ID NO: 20), GQQQLG (SEQ ID NO: 21), YGQQQLG (SEQ ID NO: 22), KKGEGS (SEQ ID NO: 23), AKAAKSS (SEQ ID NO: 24), and AKASS (SEQ ID NO: 25).

Most ideally, said N-terminal hexapeptide cross-linking sequence is selected from the group comprising: SGEGKK (SEQ ID NO: 14), SGEGK (SEQ ID NO: 15), GKK, AKAAK (SEQ ID NO: 16), AKA, SSAKAAK (SEQ ID NO: 17), SSAKA (SEQ ID NO: 18), YFKG (SEQ ID NO: 19), LKG, FKG, YLKG (SEQ ID NO: 20), GQQQLG (SEQ ID NO: 21) and YGQQQLG (SEQ ID NO: 22).

Most ideally, said C-terminal hexapeptide cross-linking sequence is selected from the group comprising: GKK, KKGEGS (SEQ ID NO: 23), AKAAK (SEQ ID NO: 16), AKA, AKAAKSS (SEQ ID NO: 24), AKASS (SEQ ID NO: 25), YFKG (SEQ ID NO: 19), LKG, FKG, YLKG (SEQ ID NO: 20), GQQQLG (SEQ ID NO: 21) and YGQQQLG (SEQ ID NO: 22).

Ideally said N or C terminal hexapeptide cross-linking sequences are used in combination with the following cross-linking enzymes: Lysyl Oxidase which reacts with lysine (K), yielding a desmosine cross-link; or Trans-glutaminase which cross-links a glutamine (Q) with a lysine (K).

Having regard to Table 1, it is preferred that N-terminal cross-linking sequences P12-13 are used with C-terminal cross-linking sequences 51-S10 and more preferably S7-S10, when the cross-linking enzyme is transglutaminase.

Further, we have observed that by combining tyrosine/DOPA rich adhesive motifs with an elastic motif, in a single polypeptide, yields an adhesive material with increased resilience and thermal stability. These observations are assumed to be as a result of the increased flexibility of the material resulting from the inclusion of an elastic motif. This adhesive is particularly advantageous when bonding joints that need to withstand flexing, such as when the bonded joint is heated or cooled.

Therefore, in yet a further preferred aspect or embodiment of the invention said adhesive hexapeptide is linked to at least one elastic conferring sequence or a sequence that confers elastomeric properties wherein said elastic conferring sequence is selected from the group comprising: GVGVAP (SEQ ID NO: 26), GGRPSDSYGAPGGGN (SEQ ID NO: 27) and KKWTWNPATGKWTWQE (SEQ ID NO: 28).

In particularly preferred embodiments said adhesive polypeptide comprises a plurality of said elastic conferring sequences or sequences that confer elastomeric properties wherein each of these sequences is provided N or C-terminal to at least one of said plurality of adhesive hexapeptide motifs.

As mentioned above, adhesive peptide degradation can be accelerated through treatment with protease enzymes or chemicals that accelerate peptide bond hydrolysis. In this respect, we have observed that by combining tyrosine/DOPA rich adhesive hexapeptide motifs with a de-bonding or cleavable motif, ideally in a single polypeptide, yields an adhesive material which can be de-bonded from a substrate. This is particularly advantageous when reversable adhesion is required.

Therefore, in yet a further preferred aspect or embodiment of the invention said adhesive hexapeptide is linked to at least one de-bonding sequence or cleavable sequence whereby said adhesive containing said plurality of hexapeptides can be de-bonded from a substrate, wherein said de-bonding sequence or cleavable sequence is selected from the group comprising:

```
                                   (SEQ ID NO: 29)
XIEGR//X
or
                                   (SEQ ID NO: 30)
XIDGR//X;
                                   (SEQ ID NO: 31)
XLEVLFQ//GPX
                                   (SEQ ID NO: 32)
XENLYFQ//SGX
                                   (SEQ ID NO: 33)
XDDDDK//X

XK//X
or

XR//X
                                   (SEQ ID NO: 34)
XΦK//ZX
or
                                   (SEQ ID NO: 35)
XΦR//ZX;

XK//X
or

XA//X
or

XY//X
```

Where X = any amino acid; Φ = A, V, L, I, F, W, or Y; and Z = any amino acid except V. // is the peptide bond that is cleaved.

The above de-bonding sequence or cleavable sequence motifs contain peptide bonds highly susceptible to hydrolysis when treated with specific enzymes. Preferably we use proteases for cleaving said sequence motifs which motifs are, advantageously, recognised only by highly specific protease enzymes, thus allowing for highly selective break down of the adhesive polymer. The above seven sequence motifs are recognised by Factor Xa protease, human rhinovirus 3C protease (HRV-3C), tobacco etch virus (TEV) protease, enterokinase (Enk) protease, trypsin protease, papain protease and bromelain protease, respectively. We have shown that digesting the adhesive peptide after curing will cause the material to break up and reduce the strength of the adhesive bond or join, so-called de-bonding.

Those skilled in the art will appreciate the invention encompasses an adhesive comprising any number or combination of the sequences listed in Table 1. Preferably in a certain embodiment at least two of the adhesive hexapeptide motifs [A1-A13] are the same. More preferably still, said adhesive further comprises any combination of said sequences in columns 2, 4, 6, 8 and 10, wherein the number of each sequence and the combination of sequences will determine the bonding strength of the adhesive, the elastomeric properties of the adhesive and the de-bonding capacity of the adhesive.

In certain embodiments of the invention said adhesive comprises at least one of the following polypeptide sequences (shown in Table 2):

SGEGKK GYYGKK GYYGKK GYYGKK (SEQ ID NO: 36) wherein said sequence comprises a N-terminal cross-linking sequence followed by three adhesive hexapeptide motifs: [P1]-$[A1]_3$, known as AP1 this polypeptide is suitable for cross-linking and so has superior bonding characteristics;

SGEGKK AYYAKK AYYAKK AYYAKK (SEQ ID NO: 37) wherein said sequence comprises a N-terminal cross-linking sequence followed by three adhesive hexapeptide motifs: [P1]-$[A2]_3$, known as AP2 this polypeptide is suitable for cross-linking and so has superior bonding characteristics;

SGEGKK GYYGKK GYYGKK GYYGKK GYYGKK GYYGKK GYYGKK (SEQ ID NO: 38) wherein said sequence comprises a N-terminal cross-linking sequence followed by six adhesive hexapeptide motifs: [P1]-$[A1]_6$, known as AP3 this polypeptide is suitable for cross-linking and so has more superior bonding characteristics;

SGEGKK GYYGKK GYYGKK GYYGKK GYYGKK GYYGKK GYYGKK GYYGKK GYYGKK GYYGKK (SEQ ID NO: 39) wherein said sequence comprises a N-terminal cross-linking sequence followed by nine adhesive hexapeptide motifs: [P1]-$[A1]_9$, known as AP6 this polypeptide is suitable for cross-linking and so has yet more superior bonding characteristics;

GYYGKK GYYGKK AYYARR GKKGYY GKKGYY AYYARR GKKGYY GKKGYY (SEQ ID NO: 40) wherein said sequence comprises eight adhesive hexapeptide motifs: [A1]2-[A8]-$[A1]_2$-[A8]-$[A1]_2$, known as AP29 this polypeptide has superior bonding characteristics; and SGEGKK AYYARR AYYARR AYYAKK (SEQ ID NO: 41) wherein said sequence comprises a N-terminal cross-linking sequence followed by three adhesive hexapeptide motifs: [P1]-$[A8]_2$-[A2], known as AP30 this polypeptide is suitable for cross-linking and so has more superior bonding characteristics.

In the following alternative embodiments of the invention, the use of cross-linking N and C terminal sequences is critical, because there is no Lysine (K) in the adhesive hexapeptide domain for cross-linking enzymes to act upon to create cross-linking. The following polypeptide sequences are shown in Table 3: AKA GYYGRR GYYGRR AKA (SEQ ID NO: 42) wherein said sequence comprises a N and C-terminal cross-linking sequences and two adhesive hexa peptide motifs: [P5]-$[A6]_2$-S4, known as AP24 this polypeptide is highly suitable for cross-linking and so has superior bonding characteristics; and AKA GYYGSS GYYGSS AKA (SEQ ID NO: 43) wherein said sequence comprises a N and C-terminal cross-linking sequences and two adhesive hexapeptide motifs: [P5]-$[A7]_2$-S4, known as AP25 this polypeptide is highly suitable for cross-linking and so has superior bonding characteristics.

Thus, the skilled person will appreciate in the afore peptide sequences the inclusion of terminal, lysine containing sequences, allow for the formation of higher molecular weight polymers via lysine cross-linking, which can be brought about enzymatically using lysine mediated cross-linking enzymes or chemically using an appropriate chemical cross-linking agent, such as a compound with two or more Michael Acceptors.

Notably AP25 is particularly suited for use in an environment in which proteases exist because the absence of lysine (K) (other than in the N or C-terminal cross-linking sequences) or arginine (R) means the peptide is less likely to be degraded by environmental proteases.

Yet further alternative aspects or embodiments of the invention, but based upon the above premise, comprise one of the following debondable or cleavable polypeptide sequences (shown in Table 4):

SGEGKK GYYGKK GYYGKK GYYGKK LEVLFQGP GYYGKK GYYGKK GYYGKK GYYGKK (SEQ ID NO: 44) wherein said sequence comprises an N-terminal cross-linking sequence, three adhesive hexapeptide motifs, a debondable region and four further adhesive hexapeptide motifs: [P1]-$[A1]_3$-[D3]-$[A1]_4$, known as ADP1 this polypeptide is highly suitable for cross-linking and so has superior bonding characteristics; or SGEGKK GYYGKK GYYGKK GYYGKK G LEVLFQGP GYYGKK GYYGKK GYYGKK GYYGKK GYY (SEQ ID NO: 45) wherein said sequence comprises an N-terminal cross-linking sequence, three adhesive hexapeptide motifs, a glycine, a de-bondable region, four further adhesive hexapeptide motifs and a tripeptide of glycine—tyrosine-tyrosine: [P1]-$[A1]_3$-[D3]-$[A1]_3$ GYY, known as ADP1[G] this polypeptide is highly suitable for cross-linking and so has superior bonding characteristics; and SGEGKK GYYGKK GYYGKK LEVLFQGP GKKGYY GKKGYY LEVLFQGP GKKGYY GKKGYY (SEQ ID NO: 46) wherein said sequence comprises an N-terminal cross-linking sequence, two adhesive hexapeptide motifs, a de-bondable region two further adhesive hexapeptide motifs a further de-bondable region, and two further adhesive hexapeptide motifs: [P1]-$[A1]_2$-[D3]-$[A5]_2$-[D3]-$[A5]_2$-[S1], known as ADP2 this polypeptide is highly suitable for cross-linking and so has superior bonding characteristics; or SGEGKK GYYGKK GYYG LEVLFQGP GKKGYY GKKGYY G LEVLFQGP GKKGYY GKKGYY GKK (SEQ ID NO: 47) wherein said sequence comprises an N-terminal cross-linking sequence, one adhesive hexapeptide motif, a GYYG sequence, a de-bondable region two further adhesive hexapeptide motifs, a glycine, a further de-bondable region, two further adhesive hexapeptide motifs and a C-terminal cross-linking sequence: [P1]-[A1]-GYYG-[D3]-$[A5]_2$-G-[D3HA5]$_2$-[S1], known as ADP2[G] this polypeptide is highly suitable for cross-linking and so has superior bonding characteristics; and SGEGKK AYYAKK ARA AYYAKK (SEQ ID NO: 48) wherein said sequence comprises an N-terminal cross-linking sequence, one adhesive hexapeptide motif, a ARA debonding sequence, and one adhesive hexapeptide motif:

[P1]-[A2]-[D9]-[A2], known as ADP5 this polypeptide is highly suitable for cross-linking and so has superior bonding characteristics; and SGEGKK GYYGKK ARA GYYGKK (SEQ ID NO: 49) wherein said sequence comprises an N-terminal cross-linking sequence, one adhesive hexapeptide motif, a ARA debonding sequence, and one adhesive hexapeptide motif: [P1]-[A1]-[D9]-[A1], known as ADP6 this polypeptide is highly suitable for cross-linking and so has superior bonding characteristics; and SGEGKK GYYGKK ENLYFQSG GYYGKK (SEQ ID NO: 50) wherein said sequence comprises an N-terminal cross-linking sequence, one adhesive hexapeptide motif, a debonding sequence, and one adhesive hexapeptide motif: [P1]-[A1]-[D4]-[A1], known as ADP7 this polypeptide is highly suitable for cross-linking and so has superior bonding characteristics; and FKG KKAYYA ARA AYYAKK GQQQLG (SEQ ID NO: 51) wherein said sequence comprises an N-terminal cross-linking sequence, one adhesive hexapeptide motif, a debonding sequence, and one adhesive hexapeptide motif and a C-terminal cross-linking sequence: [P10]-[A4]-[D9]-[A2]-[S11], known as ADP8 known as ADP-X this polypeptide is highly suitable for cross-linking and so has superior bonding characteristics; and SGEGKK GYYGRR GYYGRR LEVLFQGP GYYGRR GYYGRR GKK (SEQ ID NO: 52) wherein said sequence comprises an N-terminal cross-linking sequence, two adhesive hexapeptide motifs, a de-bondable region two further adhesive hexapeptide motifs and a C-terminal cross-linking sequence: [P1]-$[A6]_2$-[D3]-$[A6]_2$-[S1], known as ADP-X this polypeptide is highly suitable for cross-linking and so has superior bonding characteristics.

In yet a further preferred aspect or embodiment of the invention said adhesive comprises at least one elastic conferring sequence or a sequence that confers elastomeric properties such as at least one of the following polypeptide sequences (shown in Table 5):

KKGYYG KKGYYG GVGVAP GVGVAP GVGVAP GYYGKK GYYGKK (SEQ ID NO: 53) wherein said sequence comprises two adhesive hexapeptide motifs, three elastomeric sequences and two further adhesive hexapeptide sequences: $[A3]_2$-$[E1]_3$-$[A1]_2$, known as AEP1 this polypeptide is suitable for use in instances where the adhesive needs to be flexible; or G KKGYYG KKGYYG GVGVAP GVGVAP GVGVAP G GYYGKK GYYGKK (SEQ ID NO: 54) wherein said sequence comprises a glyine, two adhesive hexapeptide motifs, three elastomeric sequences, a glycine and two further adhesive hexapeptide sequences: $[A3]_2$-$[E1]_3$-[G]-$[A1]_2$, known as AEP1[G] this polypeptide is suitable for use in instances where the adhesive needs to be flexible; and SGEKK GYYGKK GYYGKK GVGVAP GVGVAP GVGVAP GYYGKK GYYGKK (SEQ ID NO: 55) wherein said sequence comprises an N-terminal cross-linking sequence, two adhesive hexapeptide motifs, three elastomeric sequences and two further adhesive hexapeptide sequences: [1P]-$[A1]_2$-$[E1]_3$-$[A1]_2$, known as AEP1b this polypeptide is suitable for use in instances where the adhesive needs to be flexible; and KKGYYG GGRPSDSYGAPGGGN GYYGKK (SEQ ID NO: 56) wherein said sequence comprises an adhesive hexapeptide motif, an elastomeric sequence and a further adhesive hexapeptide sequence: [A3]-[E2]-[A1], known as AEP3 this polypeptide is suitable for use in instances where the adhesive needs to be flexible; and KKGYYG KKWTWNPATGKWTWQE GYYGKK (SEQ ID NO: 57) wherein said sequence comprises an adhesive hexapeptide motif, an elastomeric sequence and a further adhesive hexapeptide sequence: [A3]-[E3]-[A1], known as AEP4 this polypeptide is suitable for use in instances where the adhesive needs to be flexible; and GKK GYYGKK GYYGKK GGRPSDSYGAPGGGN GGRPSDSYGAPGGGN GKKGYY GKKGYY GKK (SEQ ID NO: 58) wherein said sequence comprises an N-terminal cross-linking sequence, two adhesive hexapeptide motifs, two elastomeric sequences, two further adhesive hexapeptide motifs and GKK: [1P]-$[A1]_2$-$[E3]_2$-$[A5]_2$-[S1], known as AEP5 this polypeptide is suitable for use in instances where the adhesive needs to be flexible; and GKK GYYGKK GYYGKK KKWTWNPATGKWTWQE GKKGYY GKKGYY GKK (SEQ ID NO: 59) wherein said sequence comprises an N-terminal cross-linking sequence, two adhesive hexapeptide motifs, an elastomeric sequence, two further adhesive hexapeptide sequences and a C-terminal cross-linking sequence [P3]-$[A3]_2$-[E3]-$[A5]_2$-[S1] known as AEP7 this polypeptide is suitable for use in instances where the adhesive needs to be flexible.

In yet a further preferred aspect or embodiment of the invention said adhesive comprises at least one elastic conferring sequence or a sequence that confers elastomeric properties and at least one de-bonding region or cleavable region such as at least one of the following polypeptide sequences (shown in Table 6):

GKKGYY GKKGYY G GVGVAP LEVLFQGP GVGVAP G GYYGKK GYYGKK (SEQ ID NO: 60) wherein said sequence comprises two adhesive hexapeptide motifs, a glycine, an elastomeric sequence, a de-bonding sequence, an elastomeric sequence, a glycine and two further adhesive hexapeptide sequences: $[A5]_2$-G-[E1]-[D3]-[E1]-G-$[A1]_2$, known as AEDP1 [G] this polypeptide is suitable for use in instances where the adhesive needs to be flexible and selectively de-bonded from a substrate; or GKKGYY GKKGYY GVGVAP LEVLFQGP GVGVAP GYYGKK GYYGKK (SEQ ID NO: 61) wherein said sequence comprises two adhesive hexapeptide motifs, an elastomeric sequence, a de-bonding sequence, an elastomeric sequence, and two further adhesive hexapeptide motifs: $[A5]_2$-[E1]-[D3]-[E1]-$[A1]_2$, known as AEDP1 this polypeptide is suitable for use in instances where the adhesive needs to be flexible and selectively de-bonded from a substrate; and AKA GYYGSS GYYGSS GVGVAP LEVLFQGP GVGVAP GYYGSS GYYGSS AKA (SEQ ID NO: 62) wherein said sequence comprises an N-terminal cross-linking sequence, two adhesive hexapeptide motifs, an elastomeric sequence, a de-bonding sequence, an elastomeric sequence, two further adhesive hexapeptide sequences and a C-terminal cross-linking sequence: [P5]-$[A7]_2$-[E1]-[D3]-[E1]-$[A7]_2$, known as AEDP4 this polypeptide is suitable for use in instances where the adhesive needs to be flexible and selectively de-bonded from a substrate.

In yet a further preferred aspect or embodiment of the invention said adhesive comprises at least one sequence that could be cross-linked with transglutaminase (shown in Table 7):

FKG GYYGRR GYYGRR GQQQLG (SEQ ID NO: 63) wherein said sequence comprises an N-terminal cross-linking sequence, two adhesive hexapeptide motifs and a C-terminal cross-linking sequence: [P10]-$[A6]_2$-[S11], known as AP26 or FKG GYYGSS GYYGSS GQQQLG (SEQ ID NO: 64) wherein said sequence comprises an N-terminal cross-linking sequence, two adhesive hexapeptide motifs and a C-terminal cross-linking sequence [P10]-$[A7]_2$-[S11], known as AP27.

FKG KKGYYG KKGYYG GQQQLG (SEQ ID NO: 65) wherein said sequence comprises an N-terminal cross-linking sequence, two adhesive hexapeptide motifs and a C-terminal cross-linking sequence: [P10]-$[A3]_2$-[S11], known as AP28.

According to a yet further aspect of the invention there is provide a formulation comprising:

- a plurality of hexapeptides wherein each one has a motif comprising 3 different amino acids wherein 2 of said 3 amino acids repeat side by side to provide at least one of the following patterns:
- XX-YY- or -XX-YY where X, Y and—are any 3 different amino acids; and
- between 0.5-2% of gelatine in aqueous solution; and, optionally, Tyrosinase.

In a preferred embodiment at least two of of said hexapeptides are the same.

According to a further aspect of the invention there is provided an adhesive comprising: a plurality of hexapeptides wherein each one has a motif comprising 3 different amino acids wherein 2 of said 3 amino acids repeat side by side to provide at least one of the following patterns:

- XX-YY- or -XX-YY where X, Y and—are any 3 different amino acids; or
- the afore formulation.

In a preferred embodiment at least two of of said hexapeptides are the same.

In a preferred embodiment of the invention said adhesive or formulation comprises a plurality of adhesive hexapeptides, including any number or combination of adhesive hexapeptides herein described, preferably wherein at least two of said hexapeptides are the same.

More preferably, said adhesive or formulation comprises a plurality of adhesive hexapeptides wherein at least one of which comprises an N-terminal and/or C-terminal cross-linking sequence.

Even yet more preferably, said adhesive or formulation comprises a plurality of adhesive hexapeptides wherein a plurality of which comprise a plurality of, N-terminal and/or C-terminal crosslinking sequences.

Yet more preferably still, said adhesive or formulation comprises a plurality of adhesive hexapeptides and at least one, and ideally a plurality of, de-bonding or cleavage sequences whereby said adhesive can be de-bonded from a substrate.

Even yet more preferably, said adhesive or formulation comprises a plurality of adhesive hexapeptides and at least one, and ideally a plurality of, elastic conferring sequences or sequences that confers elastomeric properties.

Most ideally, said adhesive or formulation comprises a plurality of adhesive hexapeptides and at least one, and ideally a plurality, of de-bonding or cleavage sequences and/or at least one, and ideally a plurality, of elastic conferring sequences or sequences that confers elastomeric properties.

Most ideally, said adhesive or formulation comprises a plurality of adhesive hexapeptides and at least one, and ideally a plurality, of de-bonding or cleavage sequnces and/or at least one, and ideally a plurality, of elastic conferring sequences or sequences that confers elastomeric properties and/or at least one N-terminal or C-terminal crosslinking sequence.

As mentioned, those skilled in the art will appreciate the invention encompasses an adhesive or formulation comprising a plurality of the sequences listed in Table 1, including any number or combination thereof. Preferably, at least two of the same adhesive hexapeptides are provided. More preferably still, said adhesive or formulation comprises any combination of said sequences in columns 2, 4, 6, 8 and 10, wherein the number of each sequence and the combination of sequences will determine the bonding strength of the adhesive, the de-bonding capacity of the adhesive and the elastomeric properties of the adhesive.

Using the above sequences one can create a polypeptide sequence that will include two preferred features of the invention: one being, to reduce the lysine (K) content in the adhesive hexapeptide sequence and the other being to enable cross-links to form only through sequence motifs at the start (N terminus) and/or end (C terminus) of the hexapeptide. This is exemplified in AP24 and AP25, Table 3. Another notable feature of the invention is to omit all lysine (K) (other than when used in the N and/or C terminal cross-linking sequences) or arginine (R) from the hexapeptide motifs so that the hexapeptides, and thus the adhesives made therefrom, are less likely to be degraded by environmental proteases. This is exemplified in AP25, Table 3.

In the claims which follow and in the preceding description of the invention, except where the context requires otherwise due to express language or necessary implication, the word “comprise”, or variations such as “comprises” or “comprising” is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

An embodiment of the present invention will now be described by way of example only with reference to the following wherein:

FIG. 1A. Data showing the increase in adhesion strength of gelatine resulting from of adding adhesive peptide AEP1. P=Adhesive Peptide AEP1, P+T=Adhesive Peptide AEP1+Tyrosinase, G=Gelatine; G+T=Gelatine+Tyrosinase; P+G=Adhesive Peptide AEP1+Gelatine, P+G+T=Adhesive Peptide AEP1+Gelatine+Tyrosinase. Error bars show the standard deviation from n=5 samples.

Figure 1B:
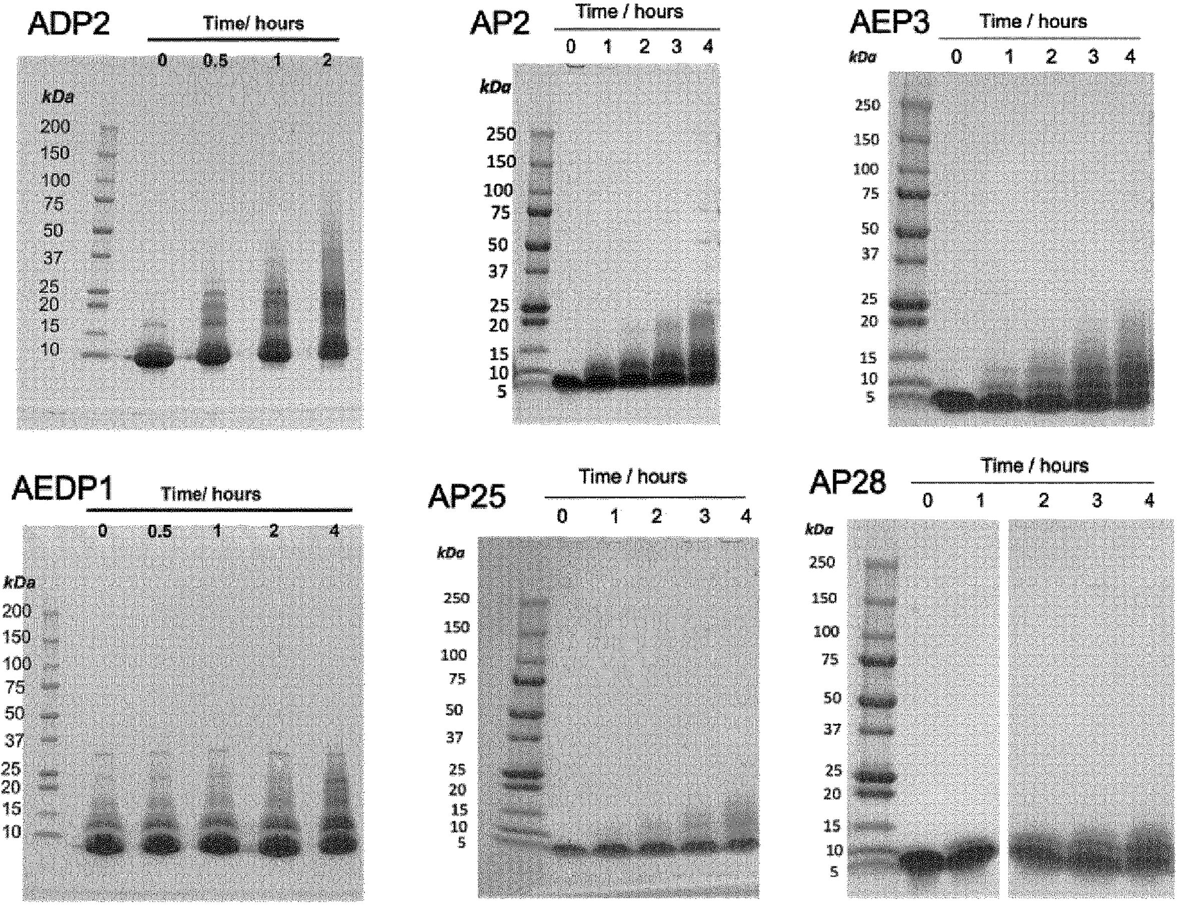

FIG. 1B. Time dependent oxidation of example adhesive hexapeptides ADP2, AP2, AEP3, AEDP1, AP25 & AP28, by tyrosinase, is shown to form high molecular weight structures through oxidative crosslinking.

Figure 2:
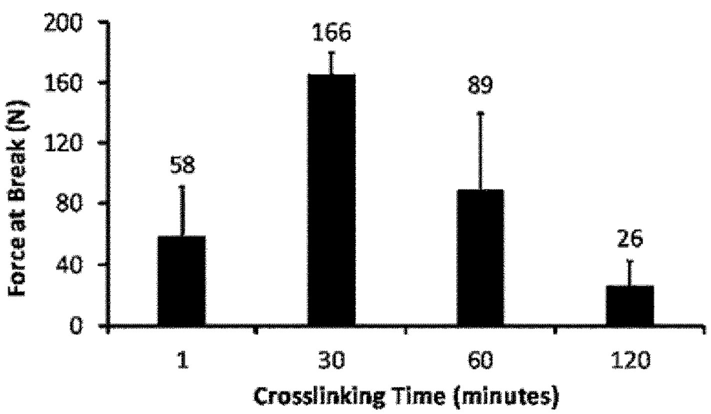

FIG. 2. Data for determining the optimal cross-linking time of the adhesive peptide (AP) mixture in the pot prior to applying to the surface. Errors have been calculated from the standard deviation (n=5).

Figure 3:
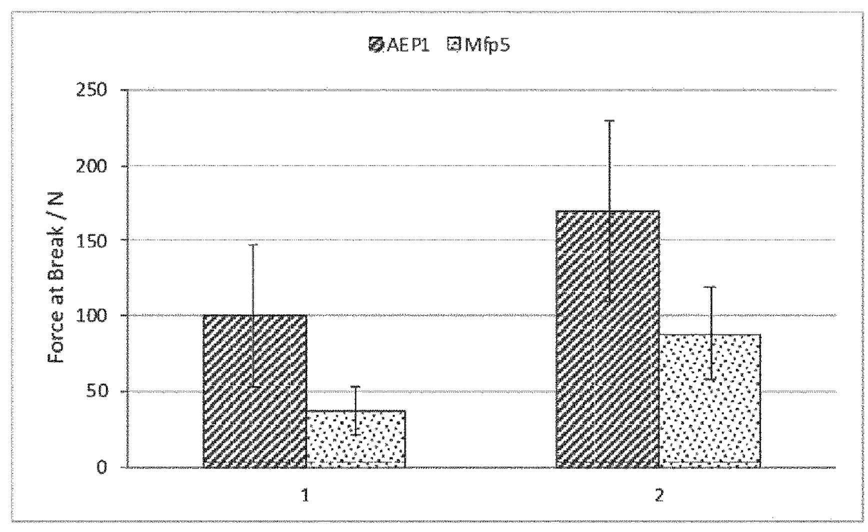

FIG. 3. Shows a comparison of AEP1 with the naturally occurring Mfp5. Data set 1 shows the force at break after cure at ambient conditions (described in methods). Data set 2 shows the force at break after heating at 150° C. for 60 minutes Errors bars show the standard deviation (n=8-10). Hash graph is test adhesive peptide AEP1 and speckle graph is mussel protein adhesive.

Figure 4A:
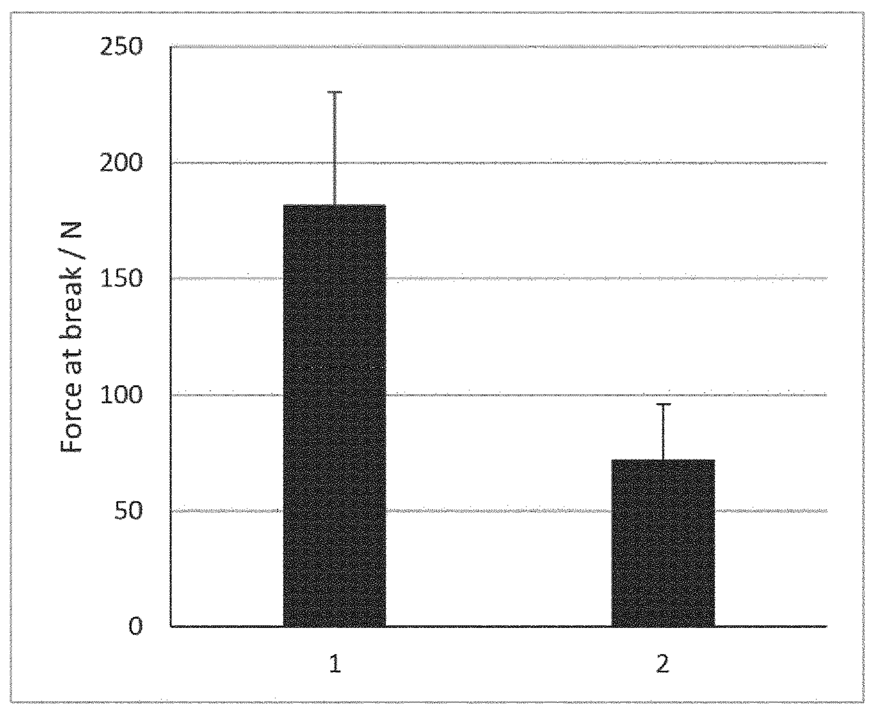

FIG. 4A. Shows debonding of AEP1, Data set 1 shows the force at break after cure at ambient conditions (described in methods). Data set 2 shows the force at break after treatment with debonding solution (described in methods). Errors bars show the standard deviation (n=6-7).

Figure 4B:
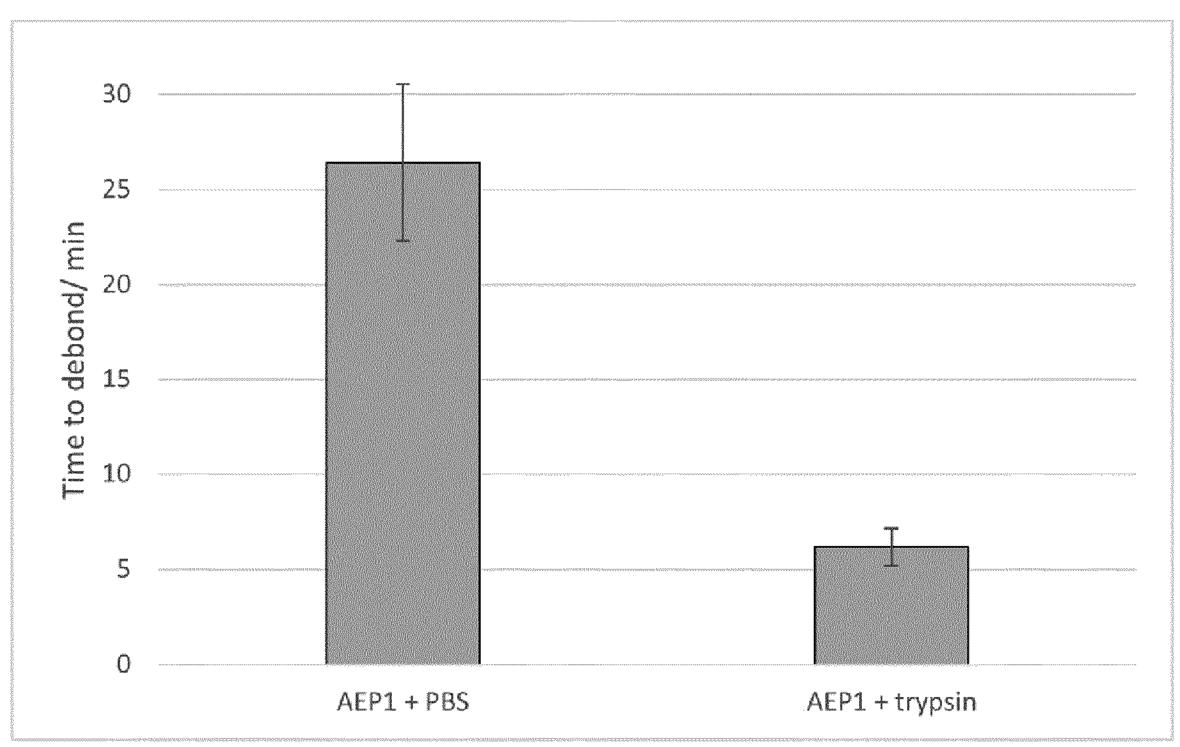

FIG. 4B. Shows the debonding performance of trypsin and PBS are compared for AEP1. The time to de-bond, after the addition of debonding agent, is significantly lower for trypsin. Error bars show the standard deviation with n=5.

Figure 4C:
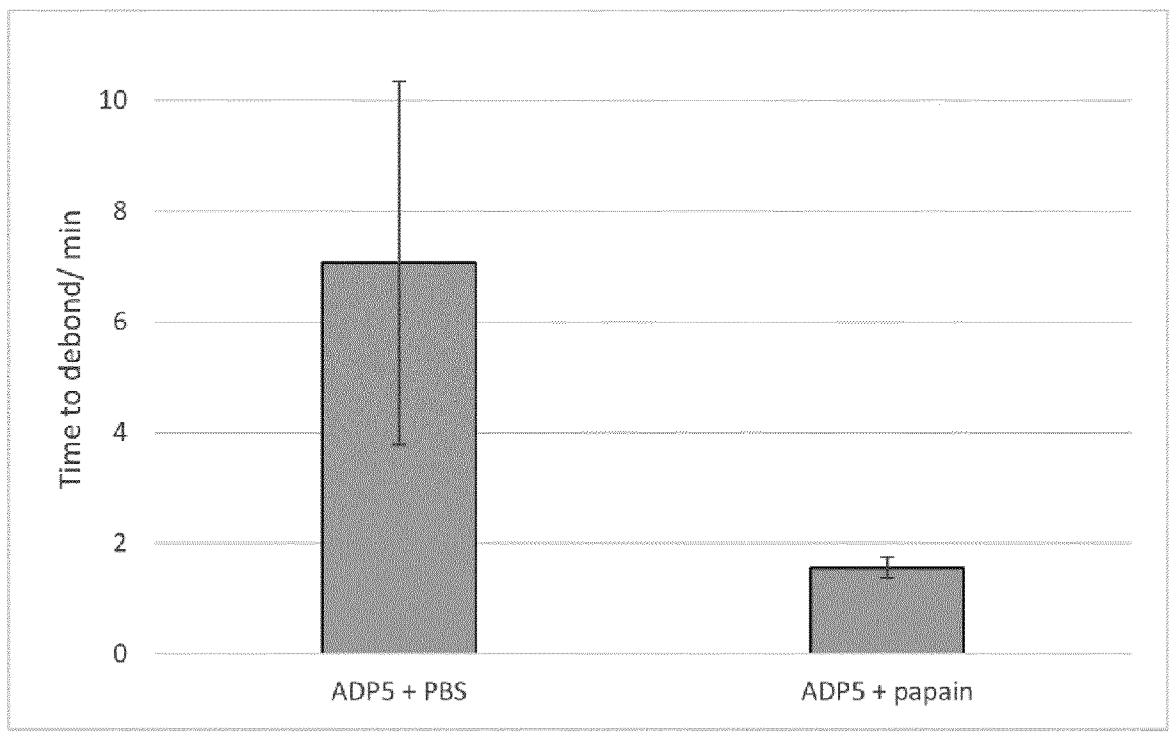

FIG. 4C. Shows the debonding performance of papain and PBS are compared for ADP5. The time to de-bond, after the addition of debonding agent, is significantly lower for papain. Error bars show the standard deviation with n=5.

Figure 5A:
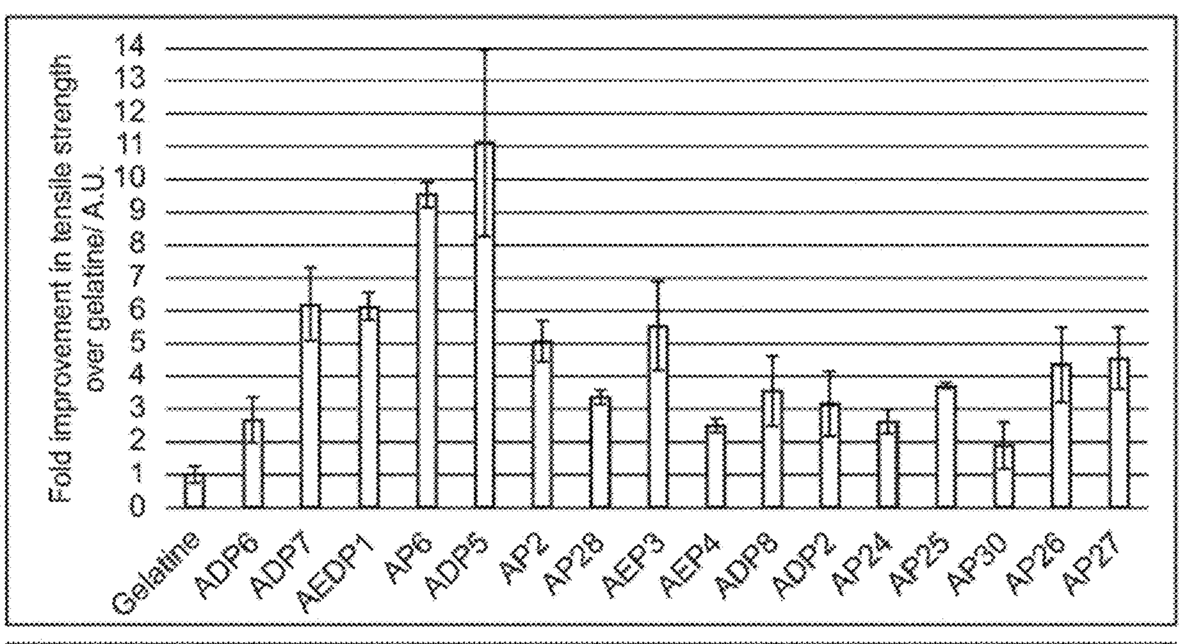

FIG. 5A. Shws the lap-shear strengths of various adhesives according to the invention are compared to gelatine. This shows that the addition to gelatine, of a variety of adhesives manufactured according to the invention, all improve upon the adhesive properties of gelatine. Error bars show the standard deviations with n=5. Tensile strength is also quoted for all peptides.

Figure 5B:
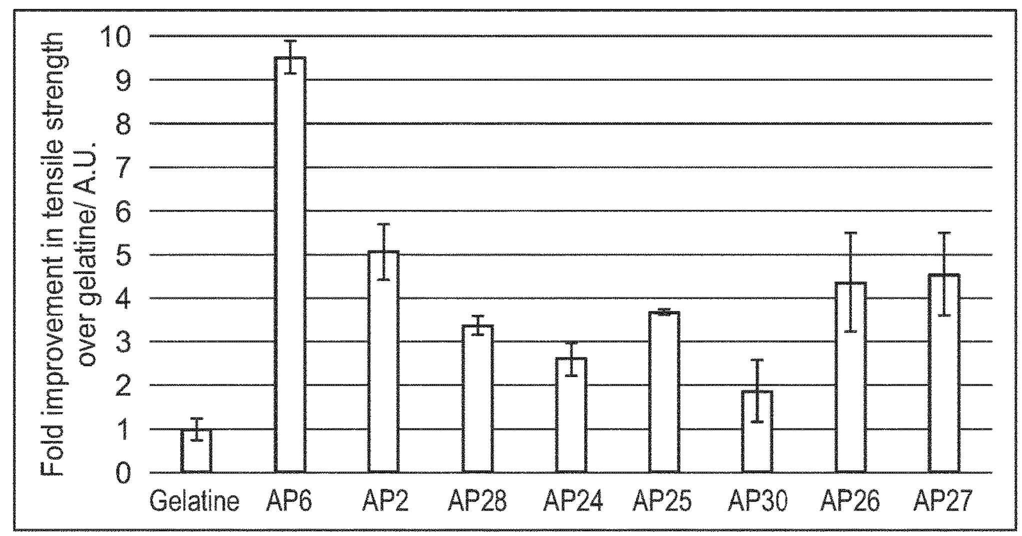

FIG. 5B. Shows the lap-shear data of FIG. 5A, presented with the adhesives grouped by function, thus showing adhesive with a different number of adhesive hexapeptides and N- or C-terminal crosslinking sequences to enable the formation of high MW structures.

Figure 5C:
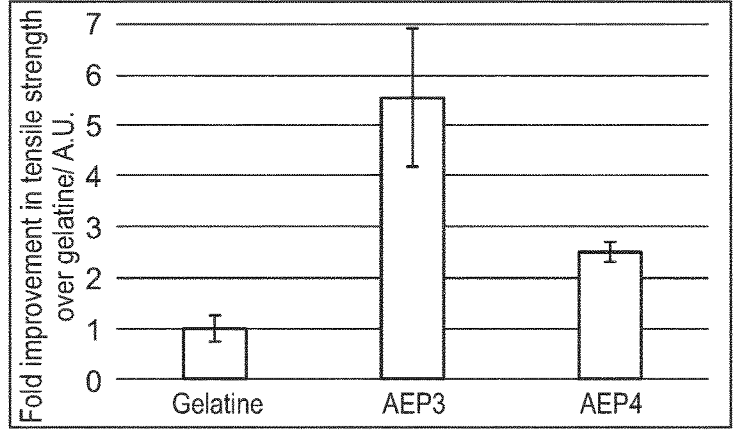

FIG. 5C. Shows the lap-shear data of FIG. 5A, showing strengths of selected elastomeric adhesives compared to gelatine. This shows that the addition, of a variety of elastic motifs all improve upon the adhesive properties of gelatine. Error bars show the standard deviations with n=5. Tensile strength is also quoted for all peptides.

Figure 5D:
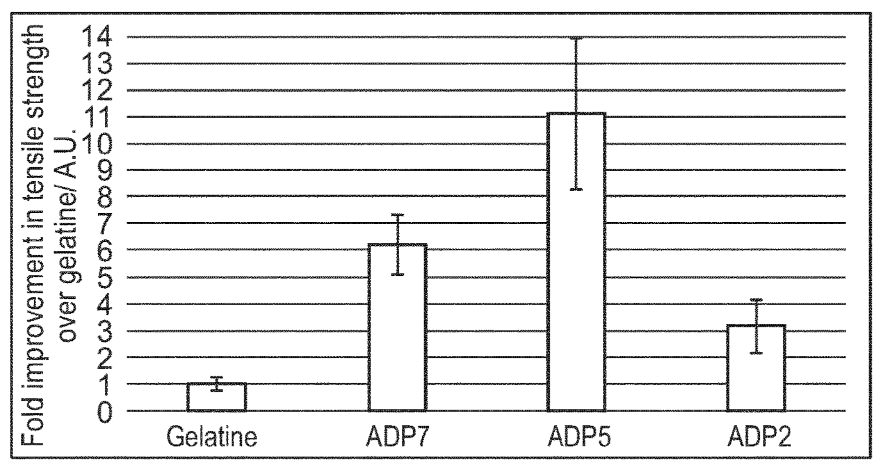

FIG. 5D. Shows the lap-shear data of FIG. 5A, showing strengths of selected debonding adhesives compared to gelatine. This shows that the addition, of a variety of debonding motifs all improve upon the debonding properties of the adhesive gelatine. Error bars show the standard deviations with n=5. Tensile strength is also quoted for all peptides.

Figure 6A:
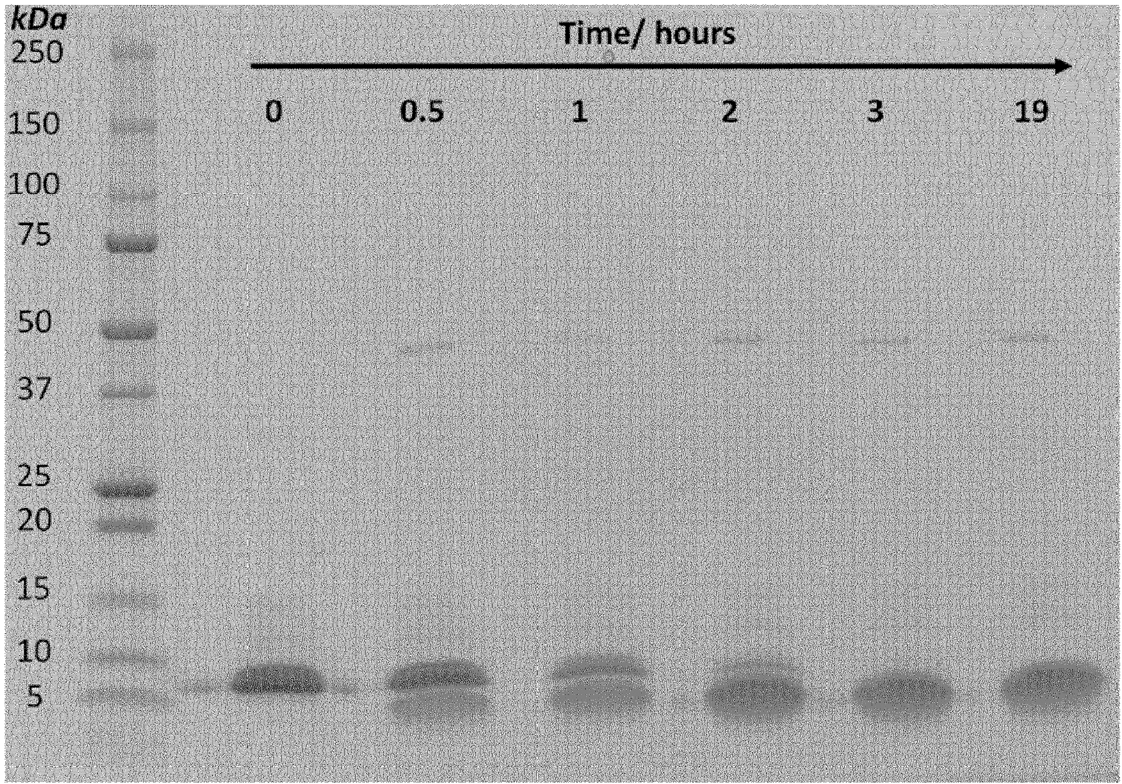
Figure 6B:
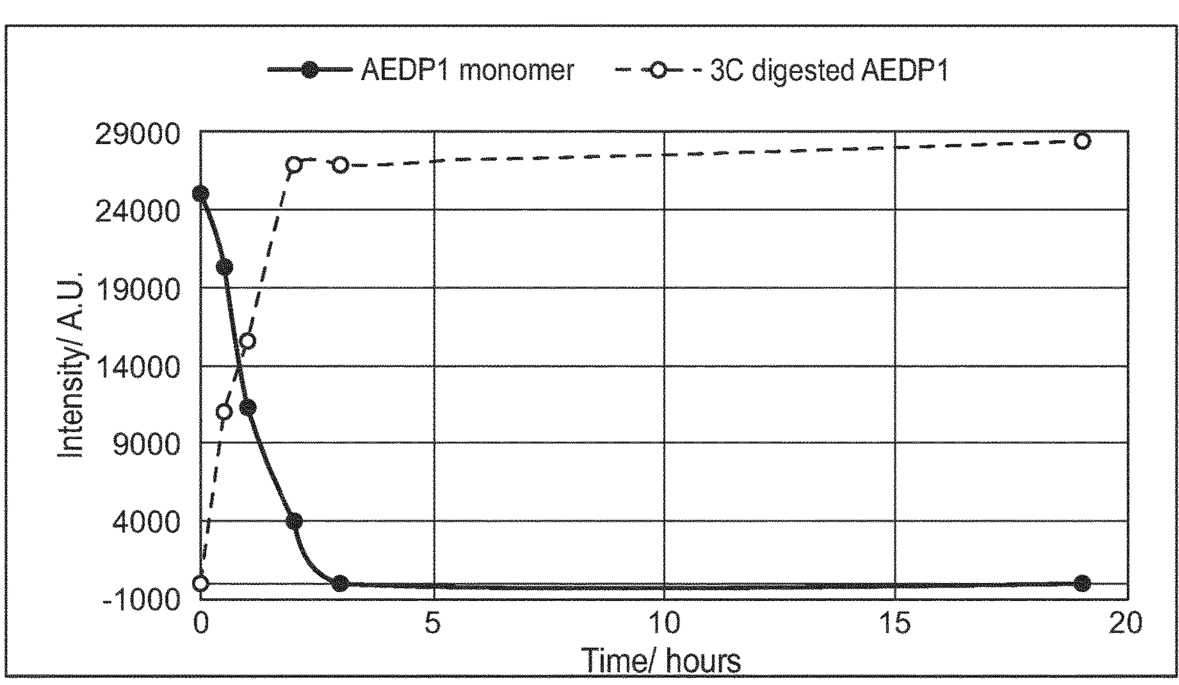
Figure 6C:
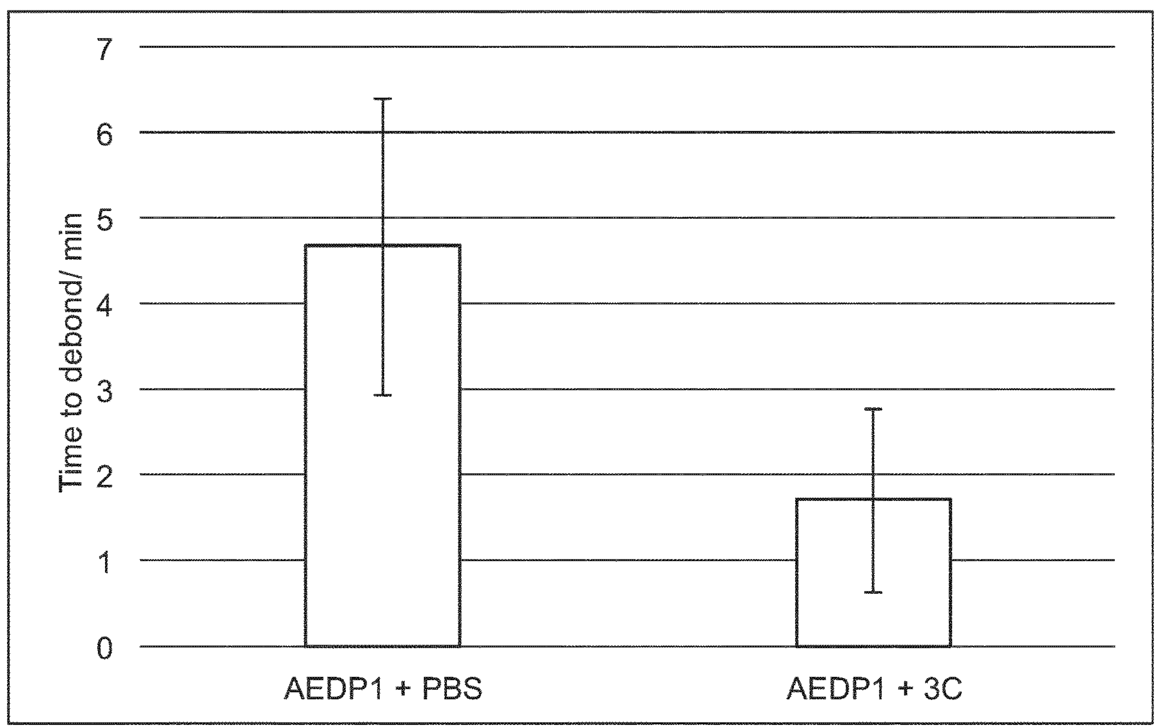

FIG. 6. A. The debonding of AEDP1 by 3C protease is shown over time. B. The debonding or digestion of AEDP1, and the formation of digested product are shown to be concomitant. C. The time to debond, after the addition of debonding agent, is lower for 3C. Error bars show the standard deviation with n=5.

Table 1: All peptide examples are made up from the 'building block' motifs presented in the table below. From the motifs presented below it is possible to generate a peptide that would have any number and/or combination of hexapeptide adhesive/de-bondable/elastic motifs. Optionally, as well, including a prefix and/or suffix motif that allows the adhesive peptide to cross-link to form higher molecular weight structures through either chemical or enzymatically induced reactions. For the De-bondable motifs X=any amino acid; Φ=A, V, L, I, F, W, or Y; and Z=any amino acid except V.

Table 2: Examples of adhesive peptides that contain any number (or combination) of the adhesive hexapeptide motifs.

Table 3: Examples of adhesive peptides that contain a prefix or suffix motif which may be required to ensure that cross-linking of peptide chains is possible.

Table 4: Examples of De-bondable Adhesives. The De-bondable sequence motif is underlined.

Table 5: Examples of Elastic Adhesives. The Elastic sequence motif is in italics.

Table 6: Examples of De-bondable Elastic Adhesives. The Elastic sequence motif is in italics and the De-bondable sequence motif is underlined.

Table 7: Examples of adhesive peptides that could be cross-linked with transglutaminase.

Methods and Materials

Peptide Production

Peptides can be sourced from commercial suppliers such as Sigma-Aldrich, Genscript, etc. Alternatively they could be produced in house using standard synthesis methods, such as solid phase synthesis, such as those described by Mollica et al., Current Bioactive Compounds, 2013, 9 184, or by recombinant methods such as those described by Mateja Zorko and Roman Jerala, Methods in Molecular Biology, 2009, 618, p 61-76.

Tyrosinase

One can use mushroom tyrosinase sourced from a supplier such as Sigma Aldrich.

Tyrosinase Cross-Linking

Tyrosinase induced crosslinking of peptides was observed by the addition of tyrosinase (0.125 units/uL) to peptide (4 mg/ml) in 25 mM ammonium acetate pH6. At time intervals, the reaction progress was monitored by SDS-PAGE analysis. 5 μL aliquots were quenched through the addition of 5 μL of 50 mM $NH_4OAc$ (pH 6) and 10 μL of 2× Laemmli sample buffer. This was then heated to 103° C. for 8 minutes and subsequently centrifuged five minutes at 14,500 rpm in a table-top centrifuge. 5 μL of each sample was analysed by SDS-PAGE.

Preparation of Adhesive Peptide Test Formulation

The test adhesive was prepared by mixing a suspension of gelatine (between 0.5-2%) in aqueous solution buffered to pH6, with the adhesive peptide (2-10 g/1). Tyrosinase (1-10 μg) was then added, the sample mixed and incubated at room temperature prior to preparation of test specimens.

Preparation of Lap Shear Test Specimens

Surfaces were prepared for adhesive experiments by washing in two consecutive acetone baths for 30 minutes followed by a single 30 minute wash in a 70% ethanol bath followed by drying in a desiccator for 16 hours. 7.5 μL of adhesive formulation (as described above) was then added to the end of a glass slide and then sandwiched by a second slide in a 3D-printed jig. A square of polythene sheet was placed between pairs of glass slides. 10 pairs of glass slides were placed in a single jig and compressed by a single 1 Kg mass, for 18 hours, at 30° C. in a Memmert UT30 plus oven.

Thermal Curing

Specimens prepared as described in the preceding paragraph and further incubated at 150° C. for 1 hour in a Memmert UT30 plus oven.

Lap Shear Testing

Lap shear tests were performed on a Shimadzu Autograph AGS-X testing machine. Samples from the above method were loaded onto the testing machine and subject to a 1 mm min-1 loading rate with a maximum load of 500 N. The breaking point force was observed with 10 technical repeats per experiment. Glass slides were prepared with a 12×26 mm overlap area based on ASTM D1002 standards.

De-Bonding by Submersion

Specimens prepared as described in the above method were submerged in a 2.5% trypsin for 30 seconds. The specimen was stored under ambient conditions for 16-24 hours before measuring the force at break using the Lap Shear test.

Time to De-Bonding of AEP1

Lap-shear specimens were loaded onto the testing machine and subject to a 1 N/sec loading rate up to a fixed load of of 30 N at which point this load was maintained. 50 μL of de-bonding agent was then added to the leading edge of the join of the lap shear specimen. The time to break was then recorded. The debonding agents used include PBS and 2.5% trypsin.

Time to De-Bonding of AEDP1

Lap-shear specimens were loaded onto the testing machine and subject to a 1 N/sec loading rate up to fixed load of 10 N AEDP1, at which point this load was maintained. μL of de-bonding agent was then added to the leading edge of the join of the lap shear specimen. The time to break was then recorded. The debonding agents used include PBS and 2.5% papain.

Time to De-Bonding of ADP5

Lap-shear specimens were loaded onto the testing machine and subject to a 1 N/sec loading rate up to fixed load of 30 N at which point this load was maintained. 50 μL of de-bonding agent was then added to the leading edge of the join of the lap shear specimen. The time to break was then recorded. The debonding agents used include PBS and 2.5% papain.

Results

Demonstrating Adhesion Promotion in a Gelatine Formulation

Our adhesive peptides are currently assessed by their ability to promote adhesion. The preparation of our test formulation is described above in 'Preparation of Adhesive Peptide Test Formulation'. The data shown in FIG. 1 show that a mixture of the peptide with or without tyrosinase does not adhere effectively under our current test conditions (samples P and P+T). Gelatin shows modest adhesion (sample G) and addition of tyrosinase does not change this adhesion strength, which is thus an important control. When adhesive peptide, gelatin and tyrosinase are mixed (sample P+G+T) we observe the benefits of our peptide as an adhesion promotor from the observed increase in adhesive strength that is greater than the sum of the individual components.

This is addition of tyrosinase acts to provide DOPA residues, by post-translationally converting tyrosine to DOPA. DOPA residues allow adhesive and cohesive interactions through surface chelation, hydrogen bonding, formation of mono, bi or tri dentate metal ion complexes and through cation-pi interactions with positively charged residues, specifically lysine (K) and arginine (R) resides. This means crosslinking occurs and the adhesive properties of the peptide are apparent. FIG. 1B shows how the addition of tyrosinase to hexapeptides ADP2, AP2, AEP3, AEDP1, AP25 & AP28 results in the formation, over time, of a high Molecular Weight complex.

Optimising Curing Time Prior to Application

Typically a 30 minute reaction time after addition of tyrosinase is optimal, prior to application of the adhesive mixture to the specimen surface (FIG. 2). Leaving the reaction for too long causes the adhesion strength to drop. The optimal 30 minute time allows DOPA to form and some cross-linking to begin. It is likely that leaving the reaction too long causes the cross-linking reaction to proceed beyond the optimal amount.

Thermal Curing Improves Performance of the Adhesive

Comparison of an exemplary adhesive peptide, AEP1, with the naturally occurring mollusk Mfp5 (FIG. 3) shows the force at break after cure at ambient conditions. The second data set shows the force at break after heating at 150° C. for 60 minutes. Errors bars show the standard deviation (n=8-10). It can be seen the curing process improves adhesive performance by about 50% for both types of adhesives.

Demonstrating Adhesion to Different Substrates

We have undertaken lap shear testing of AEP1 on a number of different substrates, including glass, stainless steel, aluminum, painted steel. A summary of the observed adhesive strength, using the lap shear method detailed above is contained in the table below.

| Substrate | Adhesive strength at break (MPa) |
|---|---|
| Glass | 0.31 |
| Stainless Steel | 0.17 |
| Aluminium | 0.16 |
| Painted Steel | 0.49 |

Demonstrating Effectiveness of De-Bonding

Debonding of AEP1 from a substrate. In FIG. 4A, data set 1, on the left, shows the force at break after cure of AEP1 adhesive at ambient conditions (described in the methods). Data set 2, on the right, shows the force at break after cure and then treatment with debonding solution (as described in the methods), Errors bars show the standard deviation (n=6-7). It can be seen that with the built-in ability to de-bond the cured adhesive requires about half the force to break the bond.

In FIG. 4B the debonding performance of trypsin and PBS are compared for AEP1. The time to de-bond, after the addition of debonding agent, is significantly lower for trypsin, showing it to be a better debonding agent for these adhesive peptides. Error bars show the standard deviation with n=5.

In FIG. 4C the debonding performance of papain and PBS are compared for ADP5. The time to de-bond, after the addition of debonding agent, is significantly lower for papain. Error bars show the standard deviation with n=5.

In FIG. 5, we show 13 different examples of adhesive peptides that show improved adhesion when compared to gelatine. This data shows that any combination of prefix (P), suffix (S), adhesive (A), elastic (E) and de-bondable (D) motif can be combined to provide an adhesive based on different peptide combinations. In FIG. 5B we show the same data but just comparing improved performance for adhesive hexpeptides {A1], [A2], [A3], [A4], [A6], [A7], [A8], [A10] and [A12]. In FIG. 5C we show the same data but just comparing improved performance for adhesive hexpeptides including elastomeric conferring sequences [E2] and [E3]. In FIG. 5*d* we show the same data but just comparing improved performance for adhesive hexpeptides including debonding sequences [D4] and [D9].

In FIG. 6 we show the digestion of AEDP1 by 3C protease over time. B. The digestion of AEDP1, and the formation of digested product are shown to be concomitant. C. The time to debond, after the addition of debonding agent, is lower for 3C, compared to trypsin. Error bars show the standard deviation with n=5.

TABLE 1

| Prefix (cross-linking) | | Adhesive | | Elastic | | De-bonding (including relevant protease) | | Suffix (cross-linking) | |
|---|---|---|---|---|---|---|---|---|---|
| P1 | SGEGKK (SEQ ID NO: 14) | A1 | GYYGKK (SEQ ID NO: 1) | E1 | GVGVAP (SEQ ID NO: 26) | D1 | IEGR (F Xa)(SEQ ID NO: 66) | S1 | GKK |
| P2 | SGEGK (SEQ ID NO: 15) | A2 | AYYAKK (SEQ ID NO: 2) | E2 | GGRPSDSYGAPGGGN (SEQ ID NO: 27) | D2 | IDGR (F Xa)(SEQ ID NO: 67) | S2 | KKGEGS (SEQ ID NO: 23) |
| P3 | GKK | A3 | KKGYYG (SEQ ID NO: 3) | E3 | KKWTWNPATGKWTWQE (SEQ ID NO: 28) | D3 | LEVLFQGP (HRV-3C) (SEQ ID NO: 68) | S3 | AKAAK (SEQ ID NO: 16) |
| P4 | AKAAK (SEQ ID NO: 16) | A4 | KKAYYA (SEQ ID NO: 4) | | | D4 | ENLYFQSG (TEV) (SEQ ID NO: 69) | S4 | AKA |
| P5 | AKA | A5 | GKKGYY (SEQ ID NO: 5) | | | D5 | DDDDK (Enk)(SEQ ID NO: 70) | S5 | AKAAKSS (SEQ ID NO: 24) |
| P6 | SSAKAAK (SEQ ID NO: 17) | A6 | GYYGRR (SEQ ID NO: 6) | | | D6 | XRX (Trypsin or Bromelain) | S6 | AKASS (SEQ ID NO: 25) |
| P7 | SSAKA (SEQ ID NO: 18) | A7 | GYYGSS (SEQ ID NO: 7) | | | D7 | XKX (Trypsin or Bromelain) | S7 | YFKG (SEQ ID NO: 19) |
| P8 | YFKG (SEQ ID NO: 19) | A8 | AYYARR (SEQ ID NO: 8) | | | D8 | XAX (Bromelain) | S8 | LKG |
| P9 | LKG | A9 | AYYASS (SEQ ID NO: 9) | | | D9 | XΦRZX (Papain)(SEQ ID NO: 34) | S9 | FKG |
| P10 | FKG | A10 | RRGYYG (SEQ ID NO: 10) | | | D10 | XΦKZX (Papain)(SEQ ID NO: 35) | S10 | YLKG (SEQ ID NO: 20) |
| P11 | YLKG (SEQ ID NO: 20) | A11 | RRAYYA (SEQ ID NO: 11) | | | | | S11 | GQQQLG (SEQ ID NO: 21) |
| P12 | GQQQLG (SEQ ID NO: 21) | A12 | SSGYYG (SEQ ID NO: 12) | | | | | S12 | YGQQQLG (SEQ ID NO: 22) |
| P13 | YGQQQLG (SEQ ID NO: 22) | A13 | SSAYYA (SEQ ID NO: 13) | | | | | | |

TABLE 2

| Name | Sequence nomenclature (by motif) | Sequence (amino acid) |
|---|---|---|
| AP1 | [P1]-[A1]$_3$ | SGEGKK GYYGKK GYYGKK GYYGKK (SEQ ID NO: 36) |
| AP2 | [P1]-[A2]$_3$ | SGEGKK AYYAKK AYYAKK AYYAKK (SEQ ID NO: 37) |
| AP3 | [P1]-[A1]$_6$ | SGEGKK GYYGKK GYYGKK GYYGKK GYYGKK GYYGKK GYYGKK (SEQ ID NO: 38) |

TABLE 2-continued

| Name | Sequence nomenclature (by motif) | Sequence (amino acid) |
|---|---|---|
| AP6 | [P1]-[A1]$_9$ | SGEGKK GYYGKK GYYGKK GYYGKK GYYGKK GYYGKK GYYGKK GYYGKK GYYGKK GYYGKK (SEQ ID NO: 39) |
| AP29 | [A1]$_2$-[A8]-[A1]$_2$-[A8]-[A1]$_2$ | GYYGKK GYYGKK AYYARR GKKGYY GKKGYY AYYARR GKKGYY GKKGYY (SEQ ID NO: 40) |
| AP30 | [P1]-[A8]$_2$-[A2] | SGEGKK AYYARR AYYARR AYYAKK (SEQ ID NO: 41) |

TABLE 3

| Name | Sequence nomenclature (by motif) | Sequence (amino acid) |
|---|---|---|
| AP24 | P5-[A6]$_2$-S4 | AKA GYYGRR GYYGRR AKA (SEQ ID NO: 42) |
| AP25 | P5-[A7]$_2$-S4 | AKA GYYGSS GYYGSS AKA (SEQ ID NO: 43) |

TABLE 4

| Name | Sequence nomenclature (by motif) | Example Sequence(s) (by amino acid) |
|---|---|---|
| ADP1 | [P1]-[A1]$_3$-[D3]-[A1]$_3$ | SGEGKK GYYGKK GYYGKK GYYGKK LEVLFQGP GYYGKK GYYGKK GYYGKK GYYGKK (SEQ ID NO: 44) SGEGKK GYYGKK GYYGKK GYYGKK G LEVLFQGP GYYGKK GYYGKK GYYGKK GYYGKK GYY (SEQ ID NO: 45) |
| ADP2 | [P1]-[A1]$_2$-[D3]-[A5]$_2$-[D3]-[A5]$_2$-[S1] | SGEGKK GYYGKK GYYGKK LEVLFQGP GKKGYY GKKGYY LEVLFQGP GKKGYY GKKGYY (SEQ ID NO: 46) SGEGKK GYYGKK GYYG LEVLFQGP GKKGYYGKKGYYGLEVLFQGP GKKGYY GKKGYY GKK (SEQ ID NO: 47) |
| ADP5 | [P1]-[A2]-[D9]-[A2] | SGEGKK AYYAKK ARA AYYAKK (SEQ ID NO: 48) |
| ADP6 | [P1]-[A1]-[D9]-[A1] | SGEGKK GYYGKK ARA GYYGKK (SEQ ID NO: 49) |
| ADP7 | [P1]-[A1]-[D4]-[A1] | SGEGKK GYYGKK ENLYFQSG GYYGKK (SEQ ID NO: 50) |
| ADP8 | [P10]-[A4]-[D9]-[A2]-[S11] | FKG KKAYYA ARA AYYAKK GQQQLG (SEQ ID NO: 51) |
| ADP-9 | [P1]-[A6]$_2$-[D3]-[A6]$_2$-[S1] | SGEGKK GYYGRR GYYGRR LEVLFQGP GYYGRR GYYGRR GKK (SEQ ID NO: 52) |

TABLE 5

| Name | Sequence nomenclature (by motif) | Example Sequence(s) (by amino acid) |
|---|---|---|
| AEP1 | [A3]$_2$-[E1]$_3$-[A1]$_2$ | G KKGYYG KKGYYG *GVGVAP GVGVAP GVGVAP* G GYYGKK GYYGKK (SEQ ID NO: 54) KKGYYG KKGYYG *GVGVAP GVGVAP GVGVAP* GYYGKK GYYGKK (SEQ ID NO: 53) |

TABLE 5-continued

| Name | Sequence nomenclature (by motif) | Example Sequence(s) (by amino acid) |
|---|---|---|
| AEP1b (with pre-fix) | [P1]-[A1]$_2$-[E1]$_3$-[A1]$_2$ | SGEKK GYYGKK GYYGKK *GVGVAP GVGVAP GVGVAP* GYYGKK GYYGKK (SEQ ID NO: 55) |
| AEP3 | [A3]-[E2]-[A1] | KKGYYG *GGRPSDSYGAPGGGN* GYYGKK (SEQ ID NO: 56) |
| AEP4 | [A3]-[E3]-[A1] | KKGYYG *KKWTWNPATGKWTWQE* GYYGKK (SEQ ID NO: 57) |
| AEP5 | [P3]-[A3]$_2$-[E2]$_2$-[A5]$_2$-[S1] | GKK GYYGKKGYYGKK *GGRPSDSYGAPGGGN GGRPSDSYGAPGGGN* GKKGYY GKKGYY GKK (SEQ ID NO: 58) |
| AEP7 | [P3]-[A3]$_2$-[E3]-[A5]$_2$-[S1] | GKK GYYGKK GYYGKK *KKWTWNPATGKWTWQE* GKKGYYGKKGYY GKK (SEQ ID NO: 59) |

TABLE 6

| Name | Sequence nomenclature (by motif) | Example Sequence(s) (by amino acid) |
|---|---|---|
| AEDP1 | [A5]$_2$-[E1]-[D3]-[E1]-[A1]$_2$ | GKKGYY GKKGYY G *GVGVAP* LEVLFQGP *GVGVAP* G GYYGKK GYYGKK (SEQ ID NO: 60) GKKGYY GKKGYY *GVGVAP* LEVLFQGP *GVGVAP* GYYGKK GYYGKK (SEQ ID NO: 61) |
| AEDP4 | [P5]-[A7]$_2$-[E1]-[D3]-[E1]-[A7]$_2$-[S4] | AKA GYYGSS GYYGSS *GVGVAP* LEVLFQGP *GVGVAP* GYYGSS GYYGSS AKA (SEQ ID NO: 62) |

TABLE 7

| Name | Sequence nomenclature (by motif) | Example Sequence(s) (by amino acid) |
|---|---|---|
| AP26 | [P10]-[A6]$_2$-[S11] | FKG GYYGRR GYYGRR GQQQLG (SEQ ID NO: 63) |
| AP27 | [P10]-[A7]$_2$-[S11] | FKG GYYGSS GYYGSS GQQQLG (SEQ ID NO: 64) |
| AP28 | [P10]-[A3]$_2$-[S11] | FKG KKGYYG KKGYYG GQQQLG (SEQ ID NO: 65) |

The invention claimed is:

1. A peptide adhesive comprising a plurality of adhesive hexapeptides wherein each adhesive hexapeptide has a motif consisting of 3 different amino acids, wherein 2 of said 3 amino acids repeat side by side to provide at least one of the following sequence pattern (s):

XX-YY- or -XX-YY wherein said hexapeptide motif is made of naturally occurring L-amino acids or D-amino acids and is selected from the group consisting of: GYYGKK (SEQ ID NO: 1), AYYAKK (SEQ ID NO: 2), KKGYYG (SEQ ID NO: 3), KKAYYA (SEQ ID NO: 4), GKKGYY (SEQ ID NO: 5), GYYGRR (SEQ ID NO: 6), GYYGSS (SEQ ID NO: 7), AYYARR (SEQ ID NO: 8), AYYASS (SEQ ID NO: 9), RRGYYG (SEQ ID NO: 10), RRAYYA (SEQ ID NO: 11), SSGYYG (SEQ ID NO: 12) and SSAYYA (SEQ ID NO: 13); and wherein, in the sequence pattern, one tyrosine (Y) is converted into 3,4-dihydroxyphenyl-L-alanine (DOPA) to give the adhesive function.

2. The peptide adhesive according to claim 1, wherein at least two of the adhesive hexapeptides are the same.

3. The peptide adhesive according to claim 1, wherein at least one adhesive hexapeptide comprises an N-terminal and/or C-terminal cross-linking sequence whereby said adhesive hexapeptide is cross-linked with other adhesive hexapeptides to provide peptide chains.

4. The peptide adhesive according to claim 3, wherein said cross-linking sequence is

SGEGKK, (SEQ ID NO: 14)

SGEGK, (SEQ ID NO: 15)

GKK, AKAAK, (SEQ ID NO: 16)

AKA, SSAKAAK, (SEQ ID NO: 17)

-continued

```
                      (SEQ ID NO: 18)
SSAKA,

                      (SEQ ID NO: 19)
YFKG,

                      (SEQ ID NO: 20)
LKG, FKG, YLKG,

                      (SEQ ID NO: 21)
GQQQLG,

                      (SEQ ID NO: 22)
YGQQQLG,

                      (SEQ ID NO: 23)
KKGEGS,

                      (SEQ ID NO: 24)
AKAAKSS, or

                      (SEQ ID NO: 25)
AKASS.
```

5. The peptide adhesive according to claim 3, wherein said N-terminal cross-linking sequence is SGEGKK (SEQ ID NO: 14), SGEGK (SEQ ID NO: 15), GKK, AKAAK (SEQ ID NO: 16), AKA, SSAKAAK (SEQ ID NO: 17), SSAKA (SEQ ID NO: 18), YFKG (SEQ ID NO: 19), LKG, FKG, YLKG (SEQ ID NO: 20), GQQQLG (SEQ ID NO: 21) or YGQQQLG (SEQ ID NO: 22).

6. The peptide adhesive according to claim 3, wherein said C-terminal cross-linking sequence is selected from the group comprising: GKK, KKGEGS (SEQ ID NO: 23), AKAAK (SEQ ID NO: 16), AKA, AKAAKSS (SEQ ID NO: 24), AKASS (SEQ ID NO: 25), YFKG (SEQ ID NO: 19), LKG, FKG, YLKG (SEQ ID NO: 20), GQQQLG (SEQ ID NO: 21) and YGQQQLG (SEQ ID NO: 22).

7. The peptide adhesive according to claim 3, wherein the N-terminal cross-linking sequence is GQQQLG (SEQ ID NO: 21) or YGQQQLG (SEQ ID NO: 22) and the C-terminal cross-linking sequence is GKK, KKGEGS (SEQ ID NO: 23), AKAAK (SEQ ID NO: 16), AKA, AKAAKSS (SEQ ID NO: 24), AKASS (SEQ ID NO: 25), YFKG (SEQ ID NO: 19), LKG, FKG or YLKG (SEQ ID NO: 20).

8. The peptide adhesive according to claim 1, wherein at least one adhesive hexapeptide is linked to at least one elastic conferring sequence or a sequence that confers elastomeric properties.

9. The peptide adhesive according to claim 8, wherein said elastic conferring sequence or a sequence that confers elastomeric properties is GVGVAP (SEQ ID NO: 26), GGRPSDSYGAPGGGN (SEQ ID NO: 27) or KKWTWNPATGKWTWQE (SEQ ID NO: 28).

10. The peptide adhesive according to claim 1, wherein at least one adhesive hexapeptide is linked to a plurality of elastic conferring sequences or sequences that confers elastomeric properties.

11. The peptide adhesive according to claim 10, wherein each of the elastic conferring sequences or sequences that confers elastomeric properties are provided N and/or C-terminal to at least one of said adhesive hexapeptides.

12. The peptide adhesive according to claim 1, wherein at least one adhesive hexapeptide is linked to at least one protease recognition sequence, whereby said peptide adhesive can be de-bonded from a substrate.

13. The peptide adhesive according to claim 12, wherein said protease recognition sequence is:

```
                      (SEQ ID NO: 29)
XIEGR//X
or
                      (SEQ ID NO: 30)
XIDGR//X;

                      (SEQ ID NO: 31)
XLEVLFQ//GPX;

                      (SEQ ID NO: 32)
XENLYFQ//SGX;

                      (SEQ ID NO: 33)
XDDDDK//X;

XK//X
or

XR//X;

                      (SEQ ID NO: 34)
XΦK//ZX
or
                      (SEQ ID NO: 35)
XΦR//ZX;
and

XK//X
or

XA//X
or

XY//X,

where X = any amino acid; Φ = A, V, L, I, F, W, or
Y; and Z = any amino acid except V and // is the
peptide bond that is cleaved.
```

14. A peptide adhesive comprising a plurality of the peptide adhesives of claim 1, wherein said peptide adhesive comprises at least one or a plurality, including any combination, of the following sequences:

```
i)
                      (SEQ ID NO: 36)
SGEGKK GYYGKK GYYGKK GYYGKK;

ii)
                      (SEQ ID NO: 37)
SGEGKK AYYAKK AYYAKK AYYAKK;

iii)
                      (SEQ ID NO: 38)
SGEGKK GYYGKK GYYGKK GYYGKK GYYGKK GYYGKK GYYGKK;

iv)
                      (SEQ ID NO: 39)
SGEGKK GYYGKK GYYGKK GYYGKK GYYGKK GYYGKK GYYGKK

GYYGKK GYYGKK GYYGKK;

v)
                      (SEQ ID NO: 40)
GYYGKK GYYGKK AYYARR GKKGYY GKKGYY AYYARR GKKGYY

GKKGYY;

vi)
                      (SEQ ID NO: 41)
SGEGKK AYYARR AYYARR AYYAKK;

vii)
                      (SEQ ID NO: 42)
AKA GYYGRR GYYGRR AKA;
```

-continued viii)

(SEQ ID NO: 43)
AKA GYYGSS GYYGSS AKA;

ix)

(SEQ ID NO: 44)
SGEGKK GYYGKK GYYGKK GYYGKK LEVLFQGP GYYGKK GYYGKK GYYGKK GYYGKK;

x)

(SEQ ID NO: 45)
SGEGKK GYYGKK GYYGKK GYYGKK G LEVLFQGP GYYGKK GYYGKK GYYGKK GYYGKK GYY;

xi)

(SEQ ID NO: 46)
SGEGKK GYYGKK GYYGKK LEVLFQGP GKKGYY GKKGYY LEVLFQGP GKKGYY GKKGYY;

xii)

(SEQ ID NO: 47)
SGEGKK GYYGKK GYYG LEVLFQGP GKKGYY GKKGYY G LEVLFQGP GKKGYY GKKGYY GKK;

xiii)

(SEQ ID NO: 48)
SGEGKK AYYAKK ARA AYYAKK;

xiv)

(SEQ ID NO: 49)
SGEGKK GYYGKK ARA GYYGKK;

xv)

(SEQ ID NO: 50)
SGEGKK GYYGKK ENLYFQSG GYYGKK;

xvi)

(SEQ ID NO: 51)
FKG KKAYYA ARA AYYAKK GQQQLG;

xvii)

(SEQ ID NO: 52)
SGEGKK GYYGRR GYYGRR LEVLFQGP GYYGRR GYYGRR GKK;

xviii)

(SEQ ID NO: 53)
KKGYYG KKGYYG GVGVAP GVGVAP GVGVAP GYYGKK GYYGKK;

xix)

(SEQ ID NO: 54)
G KKGYYG KKGYYG GVGVAP GVGVAP GVGVAP G GYYGKK GYYGKK;

xx)

(SEQ ID NO: 55)
SGEKK GYYGKK GYYGKK GVGVAP GVGVAP GVGVAP GYYGKK

-continued

GYYGKK;

xxi)

(SEQ ID NO: 56)
KKGYYG GGRPSDSYGAPGGGN GYYGKK;

xxii)

(SEQ ID NO: 57)
KKGYYG KKWTWNPATGKWTWQE GYYGKK;

xxiii)

(SEQ ID NO: 58)
GKK GYYGKK GYYGKK GGRPSDSYGAPGGGN GGRPSDSYGAPGGGN GKKGYY GKKGYY GKK;

xxiv)

(SEQ ID NO: 59)
GKK GYYGKK GYYGKK KKWTWNPATGKWTWQE GKKGYY GKKGYY GKK;

xxv)

(SEQ ID NO: 60)
GKKGYY GKKGYY G GVGVAP LEVLFQGP GVGVAP G GYYGKK GYYGKK;

xxvi)

(SEQ ID NO: 61)
GKKGYY GKKGYY GVGVAP LEVLFQGP GVGVAP GYYGKK GYYGKK;

xxvii)

(SEQ ID NO: 62)
AKA GYYGSS GYYGSS GVGVAP LEVLFQGP GVGVAP GYYGSS GYYGSS AKA;

xxviii)

(SEQ ID NO: 63)
FKG GYYGRR GYYGRR GQQQLG;

xxix)

(SEQ ID NO: 64)
FKG GYYGSS GYYGSS GQQQLG;
or xxx)

(SEQ ID NO: 65)
FKG KKGYYG KKGYYG GQQQLG.

15. A peptide adhesive comprising a plurality of the peptide adhesive(s) according to claim 14.

16. A peptide adhesive formulation comprising a plurality of adhesive peptides according to claim 1, formulated in a solution of 0.5-2% gelatin.

* * * * *

SEQUENCE LISTING

<160> NUMBER OF SEQ ID NOS: 70

<210> SEQ ID NO 1
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 1

Gly Tyr Tyr Gly Lys Lys
1 5

<210> SEQ ID NO 2
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 2

Ala Tyr Tyr Ala Lys Lys
1 5

<210> SEQ ID NO 3
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 3

Lys Lys Gly Tyr Tyr Gly
1 5

<210> SEQ ID NO 4
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 4

Lys Lys Ala Tyr Tyr Ala
1 5

<210> SEQ ID NO 5
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 5

Gly Lys Lys Gly Tyr Tyr
1 5

<210> SEQ ID NO 6
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 6

Gly Tyr Tyr Gly Arg Arg
1 5

<210> SEQ ID NO 7
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 7

-continued

Gly Tyr Tyr Gly Ser Ser
1 5

<210> SEQ ID NO 8
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 8

Ala Tyr Tyr Ala Arg Arg
1 5

<210> SEQ ID NO 9
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 9

Ala Tyr Tyr Ala Ser Ser
1 5

<210> SEQ ID NO 10
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 10

Arg Arg Gly Tyr Tyr Gly
1 5

<210> SEQ ID NO 11
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 11

Arg Arg Ala Tyr Tyr Ala
1 5

<210> SEQ ID NO 12
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 12

Ser Ser Gly Tyr Tyr Gly
1 5

<210> SEQ ID NO 13
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 13

Ser Ser Ala Tyr Tyr Ala 1 5

<210> SEQ ID NO 14
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 14

Ser Gly Glu Gly Lys Lys
1 5

<210> SEQ ID NO 15
<211> LENGTH: 5
<212> TYPE: PRT
<213> ORGANISM: Artificial Sequence
<220> FEATURE:
<223> OTHER INFORMATION: Adhesive Peptide

<400> SEQUENCE: 15

Ser Gly Glu Gly Lys
1 5

<210> SEQ ID NO 16
<211> LENGTH: 5
<212> TYPE: PRT
<213> ORGANISM: Artificial Sequence
<220> FEATURE:
<223> OTHER INFORMATION: Adhesive Peptide

<400> SEQUENCE: 16

Ala Lys Ala Ala Lys
1 5

<210> SEQ ID NO 17
<211> LENGTH: 7
<212> TYPE: PRT
<213> ORGANISM: Artificial Sequence
<220> FEATURE:
<223> OTHER INFORMATION: Adhesive Peptide

<400> SEQUENCE: 17

Ser Ser Ala Lys Ala Ala Lys
1 5

<210> SEQ ID NO 18
<211> LENGTH: 5
<212> TYPE: PRT
<213> ORGANISM: Artificial Sequence
<220> FEATURE:
<223> OTHER INFORMATION: Adhesive Peptide

<400> SEQUENCE: 18

Ser Ser Ala Lys Ala
1 5

<210> SEQ ID NO 19
<211> LENGTH: 4
<212> TYPE: PRT
<213> ORGANISM: Artificial Sequence
<220> FEATURE:
<223> OTHER INFORMATION: Adhesive Peptide

<400> SEQUENCE: 19

Tyr Phe Lys Gly
1

```
<210> SEQ ID NO 20
<211> LENGTH: 4
<212> TYPE: PRT
<213> ORGANISM: Artificial Sequence
<220> FEATURE:
<223> OTHER INFORMATION: Adhesive Peptide

<400> SEQUENCE: 20

Tyr Leu Lys Gly
1


<210> SEQ ID NO 21
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 21

Gly Gln Gln Gln Leu Gly
1               5


<210> SEQ ID NO 22
<211> LENGTH: 7
<212> TYPE: PRT
<213> ORGANISM: Artificial Sequence
<220> FEATURE:
<223> OTHER INFORMATION: Adhesive Peptide

<400> SEQUENCE: 22

Tyr Gly Gln Gln Gln Leu Gly
1               5


<210> SEQ ID NO 23
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 23

Lys Lys Gly Glu Gly Ser
1               5


<210> SEQ ID NO 24
<211> LENGTH: 7
<212> TYPE: PRT
<213> ORGANISM: Artificial Sequence
<220> FEATURE:
<223> OTHER INFORMATION: Adhesive Peptide

<400> SEQUENCE: 24

Ala Lys Ala Ala Lys Ser Ser
1               5


<210> SEQ ID NO 25
<211> LENGTH: 5
<212> TYPE: PRT
<213> ORGANISM: Artificial Sequence
<220> FEATURE:
<223> OTHER INFORMATION: Adhesive Peptide

<400> SEQUENCE: 25

Ala Lys Ala Ser Ser
1               5
```

<210> SEQ ID NO 26
<211> LENGTH: 6
<212> TYPE: PRT
<213> ORGANISM: Artificial Sequence
<220> FEATURE:
<223> OTHER INFORMATION: Adhesive Peptide

<400> SEQUENCE: 26

Gly Val Gly Val Ala Pro
1 5

<210> SEQ ID NO 27
<211> LENGTH: 15
<212> TYPE: PRT
<213> ORGANISM: Artificial Sequence
<220> FEATURE:
<223> OTHER INFORMATION: Adhesive Peptide

<400> SEQUENCE: 27

Gly Gly Arg Pro Ser Asp Ser Tyr Gly Ala Pro Gly Gly Gly Asn
1 5 10 15

<210> SEQ ID NO 28
<211> LENGTH: 16
<212> TYPE: PRT
<213> ORGANISM: Artificial Sequence
<220> FEATURE:
<223> OTHER INFORMATION: Adhesive Peptide

<400> SEQUENCE: 28

Lys Lys Trp Thr Trp Asn Pro Ala Thr Gly Lys Trp Thr Trp Gln Glu
1 5 10 15

<210> SEQ ID NO 29
<211> LENGTH: 6
<212> TYPE: PRT
<213> ORGANISM: Artificial Sequence
<220> FEATURE:
<223> OTHER INFORMATION: hexapeptide
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (5)..(6)
<223> OTHER INFORMATION: Cleavage Point
<220> FEATURE:
<221> NAME/KEY: MISC_FEATURE
<222> LOCATION: (6)..(6)
<223> OTHER INFORMATION: Xaa is any naturally occurring amino acid

<400> SEQUENCE: 29

Xaa Ile Glu Gly Arg Xaa
1 5

<210> SEQ ID NO 30
<211> LENGTH: 6
<212> TYPE: PRT
<213> ORGANISM: Artificial Sequence
<220> FEATURE:
<223> OTHER INFORMATION: Adhesive Peptide
<220> FEATURE:
<221> NAME/KEY: MISC_Feature
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (5)..(6)
<223> OTHER INFORMATION: Cleavage Point
<220> FEATURE:
<221> NAME/KEY: MISC_Feature
<222> LOCATION: (6)..(6)
<223> OTHER INFORMATION: Xaa is any naturally occurring amino acid

<400> SEQUENCE: 30

Xaa Ile Asp Gly Arg Xaa
1 5

<210> SEQ ID NO 31
<211> LENGTH: 10
<212> TYPE: PRT
<213> ORGANISM: Artificial Sequence
<220> FEATURE:
<223> OTHER INFORMATION: Adhesive Peptide
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (7)..(8)
<223> OTHER INFORMATION: Cleavage Point
<220> FEATURE:
<221> NAME/KEY: MISC_FEATURE
<222> LOCATION: (10)..(10)
<223> OTHER INFORMATION: Xaa is any naturally occurring amino acid

<400> SEQUENCE: 31

Xaa Leu Glu Val Leu Phe Gln Gly Pro Xaa
1 5 10

<210> SEQ ID NO 32
<211> LENGTH: 10
<212> TYPE: PRT
<213> ORGANISM: Artificial Sequence
<220> FEATURE:
<223> OTHER INFORMATION: Adhesive Peptide
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (7)..(8)
<223> OTHER INFORMATION: Cleavage Point
<220> FEATURE:
<221> NAME/KEY: MISC_FEATURE
<222> LOCATION: (10)..(10)
<223> OTHER INFORMATION: Xaa is any naturally occurring amino acid

<400> SEQUENCE: 32

Xaa Glu Asn Leu Tyr Phe Gln Ser Gly Xaa
1 5 10

<210> SEQ ID NO 33
<211> LENGTH: 7
<212> TYPE: PRT
<213> ORGANISM: Artificial Sequence
<220> FEATURE:
<223> OTHER INFORMATION: Adhesive Peptide
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (6)..(7)
<223> OTHER INFORMATION: Cleavage Point
<220> FEATURE:
<221> NAME/KEY: MISC_FEATURE
<222> LOCATION: (7)..(7)
<223> OTHER INFORMATION: Xaa is any naturally occurring amino acid

```
<400> SEQUENCE: 33

Xaa Asp Asp Asp Asp Lys Xaa
1               5


<210> SEQ ID NO 34
<211> LENGTH: 5
<212> TYPE: PRT
<213> ORGANISM: Artificial Sequence
<220> FEATURE:
<223> OTHER INFORMATION: Adhesive Peptide
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (2)..(2)
<223> OTHER INFORMATION: Xaa is amino acid A, V, L, I, F, W or Y
<220> FEATURE:
<221> NAME/KEY: MISC_FEATURE
<222> LOCATION: (3)..(4)
<223> OTHER INFORMATION: Cleavage point
<220> FEATURE:
<221> NAME/KEY: MISC_FEATURE
<222> LOCATION: (4)..(4)
<223> OTHER INFORMATION: Xaa is any amino acid except V
<220> FEATURE:
<221> NAME/KEY: MISC_FEATURE
<222> LOCATION: (5)..(5)
<223> OTHER INFORMATION: Xaa is any naturally occuring amino acid

<400> SEQUENCE: 34

Xaa Xaa Lys Xaa Xaa
1               5


<210> SEQ ID NO 35
<211> LENGTH: 5
<212> TYPE: PRT
<213> ORGANISM: Artificial Sequence
<220> FEATURE:
<223> OTHER INFORMATION: Adhesive Peptide
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (2)..(2)
<223> OTHER INFORMATION: Xaa is amino acid A, V, L, I, F, W or Y
<220> FEATURE:
<221> NAME/KEY: MISC_FEATURE
<222> LOCATION: (3)..(4)
<223> OTHER INFORMATION: Cleavage point
<220> FEATURE:
<221> NAME/KEY: MISC_FEATURE
<222> LOCATION: (4)..(4)
<223> OTHER INFORMATION: Xaa is any amino acid except V
<220> FEATURE:
<221> NAME/KEY: MISC_FEATURE
<222> LOCATION: (5)..(5)
<223> OTHER INFORMATION: Xaa is any naturally occurring amino acid

<400> SEQUENCE: 35

Xaa Xaa Arg Xaa Xaa
1               5


<210> SEQ ID NO 36
<211> LENGTH: 24
<212> TYPE: PRT
<213> ORGANISM: Artificial Sequence
<220> FEATURE:
<223> OTHER INFORMATION: Adhesive Peptide
```

<400> SEQUENCE: 36

```
Ser Gly Glu Gly Lys Lys Gly Tyr Tyr Gly Lys Lys Gly Tyr Tyr Gly
1               5                   10                  15

Lys Lys Gly Tyr Tyr Gly Lys Lys
            20
```

<210> SEQ ID NO 37
<211> LENGTH: 24
<212> TYPE: PRT
<213> ORGANISM: Artificial Sequence
<220> FEATURE:
<223> OTHER INFORMATION: Adhesive Peptide

<400> SEQUENCE: 37

```
Ser Gly Glu Gly Lys Lys Ala Tyr Tyr Ala Lys Lys Ala Tyr Tyr Ala
1               5                   10                  15

Lys Lys Ala Tyr Tyr Ala Lys Lys
            20
```

<210> SEQ ID NO 38
<211> LENGTH: 42
<212> TYPE: PRT
<213> ORGANISM: Artificial Sequence
<220> FEATURE:
<223> OTHER INFORMATION: Adhesive Peptide

<400> SEQUENCE: 38

```
Ser Gly Glu Gly Lys Lys Gly Tyr Tyr Gly Lys Lys Gly Tyr Tyr Gly
1               5                   10                  15

Lys Lys Gly Tyr Tyr Gly Lys Lys Gly Tyr Tyr Gly Lys Lys Gly Tyr
            20                  25                  30

Tyr Gly Lys Lys Gly Tyr Tyr Gly Lys Lys
        35                  40
```

<210> SEQ ID NO 39
<211> LENGTH: 60
<212> TYPE: PRT
<213> ORGANISM: Artificial Sequence
<220> FEATURE:
<223> OTHER INFORMATION: Adhesive Peptide

<400> SEQUENCE: 39

```
Ser Gly Glu Gly Lys Lys Gly Tyr Tyr Gly Lys Lys Gly Tyr Tyr Gly
1               5                   10                  15

Lys Lys Gly Tyr Tyr Gly Lys Lys Gly Tyr Tyr Gly Lys Lys Gly Tyr
            20                  25                  30

Tyr Gly Lys Lys Gly Tyr Tyr Gly Lys Lys Gly Tyr Tyr Gly Lys Lys
        35                  40                  45

Gly Tyr Tyr Gly Lys Lys Gly Tyr Tyr Gly Lys Lys
    50                  55                  60
```

<210> SEQ ID NO 40
<211> LENGTH: 48
<212> TYPE: PRT
<213> ORGANISM: Artificial Sequence
<220> FEATURE:
<223> OTHER INFORMATION: Adhesive Peptide

<400> SEQUENCE: 40

```
Gly Tyr Tyr Gly Lys Lys Gly Tyr Tyr Gly Lys Lys Ala Tyr Tyr Ala
1               5                   10                  15
```

```
Arg Arg Gly Lys Lys Gly Tyr Tyr Gly Lys Lys Gly Tyr Tyr Ala Tyr
            20                  25                  30

Tyr Ala Arg Arg Gly Lys Lys Gly Tyr Tyr Gly Lys Lys Gly Tyr Tyr
        35                  40                  45


<210> SEQ ID NO 41
<211> LENGTH: 24
<212> TYPE: PRT
<213> ORGANISM: Artificial Sequence
<220> FEATURE:
<223> OTHER INFORMATION: Adhesive Peptide

<400> SEQUENCE: 41

Ser Gly Glu Gly Lys Lys Ala Tyr Tyr Ala Arg Arg Ala Tyr Tyr Ala
1               5                   10                  15

Arg Arg Ala Tyr Tyr Ala Lys Lys
            20


<210> SEQ ID NO 42
<211> LENGTH: 18
<212> TYPE: PRT
<213> ORGANISM: Artificial Sequence
<220> FEATURE:
<223> OTHER INFORMATION: Adhesive Peptide

<400> SEQUENCE: 42

Ala Lys Ala Gly Tyr Tyr Gly Arg Arg Gly Tyr Tyr Gly Arg Arg Ala
1               5                   10                  15

Lys Ala


<210> SEQ ID NO 43
<211> LENGTH: 18
<212> TYPE: PRT
<213> ORGANISM: Artificial Sequence
<220> FEATURE:
<223> OTHER INFORMATION: Adhesive Peptide

<400> SEQUENCE: 43

Ala Lys Ala Gly Tyr Tyr Gly Ser Ser Gly Tyr Tyr Gly Ser Ser Ala
1               5                   10                  15

Lys Ala


<210> SEQ ID NO 44
<211> LENGTH: 56
<212> TYPE: PRT
<213> ORGANISM: Artificial Sequence
<220> FEATURE:
<223> OTHER INFORMATION: Adhesive Peptide

<400> SEQUENCE: 44

Ser Gly Glu Gly Lys Lys Gly Tyr Tyr Gly Lys Lys Gly Tyr Tyr Gly
1               5                   10                  15

Lys Lys Gly Tyr Tyr Gly Lys Lys Leu Glu Val Leu Phe Gln Gly Pro
            20                  25                  30

Gly Tyr Tyr Gly Lys Lys Gly Tyr Tyr Gly Lys Lys Gly Tyr Tyr Gly
        35                  40                  45

Lys Lys Gly Tyr Tyr Gly Lys Lys
    50                  55


<210> SEQ ID NO 45
<211> LENGTH: 60
<212> TYPE: PRT
<213> ORGANISM: Artificial Sequence
```

```
<220> FEATURE:
<223> OTHER INFORMATION: Adhesive Peptide

<400> SEQUENCE: 45

Ser Gly Glu Gly Lys Lys Gly Tyr Tyr Gly Lys Lys Gly Tyr Tyr Gly
1               5                   10                  15

Lys Lys Gly Tyr Tyr Gly Lys Lys Gly Leu Glu Val Leu Phe Gln Gly
            20                  25                  30

Pro Gly Tyr Tyr Gly Lys Lys Gly Tyr Tyr Gly Lys Lys Gly Tyr Tyr
        35                  40                  45

Gly Lys Lys Gly Tyr Tyr Gly Lys Lys Gly Tyr Tyr
    50                  55                  60


<210> SEQ ID NO 46
<211> LENGTH: 58
<212> TYPE: PRT
<213> ORGANISM: Artificial Sequence
<220> FEATURE:
<223> OTHER INFORMATION: Adhesive Peptide

<400> SEQUENCE: 46

Ser Gly Glu Gly Lys Lys Gly Tyr Tyr Gly Lys Lys Gly Tyr Tyr Gly
1               5                   10                  15

Lys Lys Leu Glu Val Leu Phe Gln Gly Pro Gly Lys Lys Gly Tyr Tyr
            20                  25                  30

Gly Lys Lys Gly Tyr Tyr Leu Glu Val Leu Phe Gln Gly Pro Gly Lys
        35                  40                  45

Lys Gly Tyr Tyr Gly Lys Lys Gly Tyr Tyr
    50                  55


<210> SEQ ID NO 47
<211> LENGTH: 60
<212> TYPE: PRT
<213> ORGANISM: Artificial Sequence
<220> FEATURE:
<223> OTHER INFORMATION: Adhesive Peptide

<400> SEQUENCE: 47

Ser Gly Glu Gly Lys Lys Gly Tyr Tyr Gly Lys Lys Gly Tyr Tyr Gly
1               5                   10                  15

Leu Glu Val Leu Phe Gln Gly Pro Gly Lys Lys Gly Tyr Tyr Gly Lys
            20                  25                  30

Lys Gly Tyr Tyr Gly Leu Glu Val Leu Phe Gln Gly Pro Gly Lys Lys
        35                  40                  45

Gly Tyr Tyr Gly Lys Lys Gly Tyr Tyr Gly Lys Lys
    50                  55                  60


<210> SEQ ID NO 48
<211> LENGTH: 21
<212> TYPE: PRT
<213> ORGANISM: Artificial Sequence
<220> FEATURE:
<223> OTHER INFORMATION: Adhesive Peptide

<400> SEQUENCE: 48

Ser Gly Glu Gly Lys Lys Ala Tyr Tyr Ala Lys Lys Ala Arg Ala Ala
1               5                   10                  15

Tyr Tyr Ala Lys Lys
            20


<210> SEQ ID NO 49
```

<211> LENGTH: 21
<212> TYPE: PRT
<213> ORGANISM: Artificial Sequence
<220> FEATURE:
<223> OTHER INFORMATION: Adhesive Peptide

<400> SEQUENCE: 49

```
Ser Gly Glu Gly Lys Lys Gly Tyr Tyr Gly Lys Lys Ala Arg Ala Gly
1               5                   10                  15

Tyr Tyr Gly Lys Lys
            20
```

<210> SEQ ID NO 50
<211> LENGTH: 26
<212> TYPE: PRT
<213> ORGANISM: Artificial Sequence
<220> FEATURE:
<223> OTHER INFORMATION: Adhesive Peptide

<400> SEQUENCE: 50

```
Ser Gly Glu Gly Lys Lys Gly Tyr Tyr Gly Lys Lys Glu Asn Leu Tyr
1               5                   10                  15

Phe Gln Ser Gly Gly Tyr Tyr Gly Lys Lys
            20                  25
```

<210> SEQ ID NO 51
<211> LENGTH: 24
<212> TYPE: PRT
<213> ORGANISM: Artificial Sequence
<220> FEATURE:
<223> OTHER INFORMATION: Adhesive Peptide

<400> SEQUENCE: 51

```
Phe Lys Gly Lys Lys Ala Tyr Tyr Ala Ala Arg Ala Ala Tyr Tyr Ala
1               5                   10                  15

Lys Lys Gly Gln Gln Gln Leu Gly
            20
```

<210> SEQ ID NO 52
<211> LENGTH: 41
<212> TYPE: PRT
<213> ORGANISM: Artificial Sequence
<220> FEATURE:
<223> OTHER INFORMATION: Adhesive Peptide

<400> SEQUENCE: 52

```
Ser Gly Glu Gly Lys Lys Gly Tyr Tyr Gly Arg Arg Gly Tyr Tyr Gly
1               5                   10                  15

Arg Arg Leu Glu Val Leu Phe Gln Gly Pro Gly Tyr Tyr Gly Arg Arg
            20                  25                  30

Gly Tyr Tyr Gly Arg Arg Gly Lys Lys
        35                  40
```

<210> SEQ ID NO 53
<211> LENGTH: 42
<212> TYPE: PRT
<213> ORGANISM: Artificial Sequence
<220> FEATURE:
<223> OTHER INFORMATION: Adhesive Peptide

<400> SEQUENCE: 53

```
Lys Lys Gly Tyr Tyr Gly Lys Lys Gly Tyr Tyr Gly Gly Val Gly Val
1               5                   10                  15

Ala Pro Gly Val Gly Val Ala Pro Gly Val Gly Val Ala Pro Gly Tyr
```

```
            20                  25                  30

Tyr Gly Lys Lys Gly Tyr Tyr Gly Lys Lys
        35                  40


<210> SEQ ID NO 54
<211> LENGTH: 44
<212> TYPE: PRT
<213> ORGANISM: Artificial Sequence
<220> FEATURE:
<223> OTHER INFORMATION: Adhesive Peptide

<400> SEQUENCE: 54

Gly Lys Lys Gly Tyr Tyr Gly Lys Lys Gly Tyr Tyr Gly Gly Val Gly
1               5                   10                  15

Val Ala Pro Gly Val Gly Val Ala Pro Gly Val Gly Val Ala Pro Gly
            20                  25                  30

Gly Tyr Tyr Gly Lys Lys Gly Tyr Tyr Gly Lys Lys
        35                  40


<210> SEQ ID NO 55
<211> LENGTH: 47
<212> TYPE: PRT
<213> ORGANISM: Artificial Sequence
<220> FEATURE:
<223> OTHER INFORMATION: Adhesive Peptide

<400> SEQUENCE: 55

Ser Gly Glu Lys Lys Gly Tyr Tyr Gly Lys Lys Gly Tyr Tyr Gly Lys
1               5                   10                  15

Lys Gly Val Gly Val Ala Pro Gly Val Gly Val Ala Pro Gly Val Gly
            20                  25                  30

Val Ala Pro Gly Tyr Tyr Gly Lys Lys Gly Tyr Tyr Gly Lys Lys
        35                  40                  45


<210> SEQ ID NO 56
<211> LENGTH: 27
<212> TYPE: PRT
<213> ORGANISM: Artificial Sequence
<220> FEATURE:
<223> OTHER INFORMATION: Adhesive Peptide

<400> SEQUENCE: 56

Lys Lys Gly Tyr Tyr Gly Gly Gly Arg Pro Ser Asp Ser Tyr Gly Ala
1               5                   10                  15

Pro Gly Gly Gly Asn Gly Tyr Tyr Gly Lys Lys
            20                  25


<210> SEQ ID NO 57
<211> LENGTH: 28
<212> TYPE: PRT
<213> ORGANISM: Artificial Sequence
<220> FEATURE:
<223> OTHER INFORMATION: Adhesive Peptide

<400> SEQUENCE: 57

Lys Lys Gly Tyr Tyr Gly Lys Lys Trp Thr Trp Asn Pro Ala Thr Gly
1               5                   10                  15

Lys Trp Thr Trp Gln Glu Gly Tyr Tyr Gly Lys Lys
            20                  25


<210> SEQ ID NO 58
<211> LENGTH: 60
<212> TYPE: PRT
```

```
<213> ORGANISM: Artificial Sequence
<220> FEATURE:
<223> OTHER INFORMATION: Adhesive Peptide

<400> SEQUENCE: 58

Gly Lys Lys Gly Tyr Tyr Gly Lys Lys Gly Tyr Tyr Gly Lys Lys Gly
1               5                   10                  15

Gly Arg Pro Ser Asp Ser Tyr Gly Ala Pro Gly Gly Gly Asn Gly Gly
            20                  25                  30

Arg Pro Ser Asp Ser Tyr Gly Ala Pro Gly Gly Gly Asn Gly Lys Lys
        35                  40                  45

Gly Tyr Tyr Gly Lys Lys Gly Tyr Tyr Gly Lys Lys
    50                  55                  60


<210> SEQ ID NO 59
<211> LENGTH: 46
<212> TYPE: PRT
<213> ORGANISM: Artificial Sequence
<220> FEATURE:
<223> OTHER INFORMATION: Adhesive Peptide

<400> SEQUENCE: 59

Gly Lys Lys Gly Tyr Tyr Gly Lys Lys Gly Tyr Tyr Gly Lys Lys Lys
1               5                   10                  15

Lys Trp Thr Trp Asn Pro Ala Thr Gly Lys Trp Thr Trp Gln Glu Gly
            20                  25                  30

Lys Lys Gly Tyr Tyr Gly Lys Lys Gly Tyr Tyr Gly Lys Lys
        35                  40                  45


<210> SEQ ID NO 60
<211> LENGTH: 46
<212> TYPE: PRT
<213> ORGANISM: Artificial Sequence
<220> FEATURE:
<223> OTHER INFORMATION: Adhesive Peptide

<400> SEQUENCE: 60

Gly Lys Lys Gly Tyr Tyr Gly Lys Lys Gly Tyr Tyr Gly Gly Val Gly
1               5                   10                  15

Val Ala Pro Leu Glu Val Leu Phe Gln Gly Pro Gly Val Gly Val Ala
            20                  25                  30

Pro Gly Gly Tyr Tyr Gly Lys Lys Gly Tyr Tyr Gly Lys Lys
        35                  40                  45


<210> SEQ ID NO 61
<211> LENGTH: 44
<212> TYPE: PRT
<213> ORGANISM: Artificial Sequence
<220> FEATURE:
<223> OTHER INFORMATION: Adhesive Peptide

<400> SEQUENCE: 61

Gly Lys Lys Gly Tyr Tyr Gly Lys Lys Gly Tyr Tyr Gly Val Gly Val
1               5                   10                  15

Ala Pro Leu Glu Val Leu Phe Gln Gly Pro Gly Val Gly Val Ala Pro
            20                  25                  30

Gly Tyr Tyr Gly Lys Lys Gly Tyr Tyr Gly Lys Lys
        35                  40


<210> SEQ ID NO 62
<211> LENGTH: 50
<212> TYPE: PRT
```

<213> ORGANISM: Artificial Sequence
<220> FEATURE:
<223> OTHER INFORMATION: Adhesive Peptide

<400> SEQUENCE: 62

Ala Lys Ala Gly Tyr Tyr Gly Ser Ser Gly Tyr Tyr Gly Ser Ser Gly
1               5                   10                  15

Val Gly Val Ala Pro Leu Glu Val Leu Phe Gln Gly Pro Gly Val Gly
            20                  25                  30

Val Ala Pro Gly Tyr Tyr Gly Ser Ser Gly Tyr Tyr Gly Ser Ser Ala
        35                  40                  45

Lys Ala
    50

<210> SEQ ID NO 63
<211> LENGTH: 21
<212> TYPE: PRT
<213> ORGANISM: Artificial Sequence
<220> FEATURE:
<223> OTHER INFORMATION: Adhesive Peptide

<400> SEQUENCE: 63

Phe Lys Gly Gly Tyr Tyr Gly Arg Arg Gly Tyr Tyr Gly Arg Arg Gly
1               5                   10                  15

Gln Gln Gln Leu Gly
            20

<210> SEQ ID NO 64
<211> LENGTH: 21
<212> TYPE: PRT
<213> ORGANISM: Artificial Sequence
<220> FEATURE:
<223> OTHER INFORMATION: Adhesive Peptide

<400> SEQUENCE: 64

Phe Lys Gly Gly Tyr Tyr Gly Ser Ser Gly Tyr Tyr Gly Ser Ser Gly
1               5                   10                  15

Gln Gln Gln Leu Gly
            20

<210> SEQ ID NO 65
<211> LENGTH: 21
<212> TYPE: PRT
<213> ORGANISM: Artificial Sequence
<220> FEATURE:
<223> OTHER INFORMATION: adhesive

<400> SEQUENCE: 65

Phe Lys Gly Lys Lys Gly Tyr Tyr Gly Lys Lys Gly Tyr Tyr Gly Gly
1               5                   10                  15

Gln Gln Gln Leu Gly
            20

<210> SEQ ID NO 66
<211> LENGTH: 4
<212> TYPE: PRT
<213> ORGANISM: Artificial Sequence
<220> FEATURE:
<223> OTHER INFORMATION: hexapeptide

<400> SEQUENCE: 66

Ile Glu Gly Arg
1

-continued

```
<210> SEQ ID NO 67
<211> LENGTH: 4
<212> TYPE: PRT
<213> ORGANISM: Artificial Sequence
<220> FEATURE:
<223> OTHER INFORMATION: Adhesive Peptide

<400> SEQUENCE: 67

Ile Asp Gly Arg
1


<210> SEQ ID NO 68
<211> LENGTH: 8
<212> TYPE: PRT
<213> ORGANISM: Artificial Sequence
<220> FEATURE:
<223> OTHER INFORMATION: Adhesive Peptide

<400> SEQUENCE: 68

Leu Glu Val Leu Phe Gln Gly Pro
1               5


<210> SEQ ID NO 69
<211> LENGTH: 8
<212> TYPE: PRT
<213> ORGANISM: Artificial Sequence
<220> FEATURE:
<223> OTHER INFORMATION: Adhesive Peptide

<400> SEQUENCE: 69

Glu Asn Leu Tyr Phe Gln Ser Gly
1               5


<210> SEQ ID NO 70
<211> LENGTH: 5
<212> TYPE: PRT
<213> ORGANISM: Artificial Sequence
<220> FEATURE:
<223> OTHER INFORMATION: Adhesive Peptide

<400> SEQUENCE: 70

Asp Asp Asp Asp Lys
1               5
```